(12) United States Patent
Chin

(10) Patent No.: US 7,214,771 B2
(45) Date of Patent: May 8, 2007

(54) NUCLEIC ACID AND PROTEIN EXPRESSION THEREBY AND THEIR INVOLVEMENT IN STRESS

(75) Inventor: Khew-Voon Chin, Highland Park, NJ (US)

(73) Assignee: University of Medicine & Dentistry of New Jersey, New Brunswick, NJ (US)

( * ) Notice: Subject to any disclaimer, the term of this patent is extended or adjusted under 35 U.S.C. 154(b) by 779 days.

(21) Appl. No.: 10/164,359

(22) Filed: Jun. 6, 2002

(65) Prior Publication Data

US 2003/0012776 A1    Jan. 16, 2003

Related U.S. Application Data

(63) Continuation of application No. PCT/US00/33438, filed on Dec. 7, 2000.

(60) Provisional application No. 60/169,418, filed on Dec. 7, 1999.

(51) Int. Cl.
*C07K 14/00* (2006.01)
(52) U.S. Cl. .................................................. 530/350
(58) Field of Classification Search ................. 530/300, 530/350
See application file for complete search history.

(56) References Cited

OTHER PUBLICATIONS

Bossone et al., Proc. Natl. Acad. Sci. USA, Aug. 15, 1992;89(16):7452-6.*
Fedele, et al., Journal of Biological Chemistry, 2000, 275:7849-7901.
Mastrangelo, et al., Oncogene, 2000, 19:3799-3804.

* cited by examiner

*Primary Examiner*—Misook Yu
(74) *Attorney, Agent, or Firm*—Klauber & Jackson

(57) ABSTRACT

The present invention pertains to a novel BTB-POZ domain zinc finger protein, which is named herein RIα-associated zinc finger (RIAZ). The nucleic acid and corresponding protein products have been identified, as have numerous diagnostic and therapeutic utilities predicated on the observed role that the factors play as mediators of the progression of several cancers, and the host response to multiple stress. We have cloned and sequenced the full length cDNA of the gene expressing this protein. We demonstrate that in vitro synthesized RIAZ protein interacts with RIα. We hypothesize that the interaction of RIα with RIAZ may regulate apoptosis, cell growth and drug resistance. The factors of the invention are also believed to play a role in host chemosensitivity to cancer drugs, and the invention extends to the modulation of the factors to treat conditions reflective of abnormal levels thereof. Also, the factors may be included in diagnostic assays, including drug discovery assays, to identify patient condition and progression during cancer therapy, as well as to identify possible new anticancer agents.

2 Claims, 15 Drawing Sheets

| POSITIONS | 1   4   8   14  17  21 |   |
|---|---|---|
| CONSENSUS | C--C---F-----L--H---H--- |   |
| Finger 1 | 294 | CGLCGKVFTDANRLRQHEAQHGVT | 317 |
| Finger 2 | 357 | CEICGKIFRDVYHLNRHKLSHSGE | 380 |
| Finger 3 | 385 | CPVCGLRFKRKDRMSYHVRSHDGS | 408 |
| Finger 4 | 415 | CQSCGKGFSRPDHLNGHIKQVHTS | 438 |
| Finger 5 | 444 | CQTCNASFATRDRLRSHLACHEDK | 467 |
| Finger 6 | 469 | CQVCGKYLRAAYMADHLKKHSEGP | 493 |
| Finger 7 | 561 | CPECGSFFRSKSYLNKHIQKVHVR | 584 |

FIG.6B

```
RIAZ   22 HSTEMIHNINQQRKNEGRFCDVLLRVGDESFPAHRAVLAACSEYFESVESAQLGDGGAADGGPADV
MIZ-1   6 HSQHVLEQLNQQRQLCLL--CDCTFVVDGVHFKAHKAVLAACSEYFKMLFVDQKDV
BCL-6  14 HASDVLLNLNRLRSRDILT-DVVIVVSREQFRAHKTVLMACSGLFYSIFTDQLKCNLSV
PLZF   16 HPTGLLCKANQMRLAGTL--CDVVIMVDSQEFFAHRTVLACTSKMFEILFHRNSQHY
ZF5    18 HKTLFIKTLNEQRLEGEF--CDIAIVVEDVKFRAHRCVLAACSTYFKKLFKKLEVDSSS
KUP     5 HSLVTLIQQLNMQREFCFLL-CDCTVAIGDVYFKAHRAVLAAFSNYFKMIFIHCTSECIKIQPTDIQP
APM-1  16 HS SEVICSLNEQRHDCII--CDVLLVVQEQEYRTHRSVLAACSKYFKKLETAGTLASQPYVY
ZID    14 QQGDVVLQKWNLLRQQNIFCDVSYINDTEFQGHKVILAACSTFMRDQFLLTQSKHV

RIAZ   84 GGATAAPGGGAGGSSRELEMHTISSKVEGDIIDFAYLSRIVVRLESFPELMTEAAKFILMRSVIEIC
MIZ-1  60                   VHLDIVSNAAGLGQMIEFMYLLAKILSLSPENVDDVTAVATFLQMQDIITAC
BCL-6  72                   INLDPEINPEGECILIIDFMYISRINLREGNIMAVMATAMYLQMEHVVDTC
PLZF   71                        TLDFLSPKTFQQILEYAYTATLQAKAEDLDDLLYAAEIEIEYLEEQC
ZF5    75                   VIEIDFLRSDIFEEVLNYMYTAKISVKKEDVNLMMSSGQIEGIRFLDKLC
KUP    71                        DIFSYLHIMYTGKGPKQIVDHSRLEEGIRFLHADYLSHIA
APM-1  76                             EIDFVQPEALAAIEFAYTSTLTITAGNVKHILNAARMLEIQCIVNVC
ZID    71                RITILQSAEVGRKLLLSCYTGAIEVKRKELLKYILTAASYLQMVHIVEKC
```

FIG. 9A

```
GTCAAAGTATGGGATTCACTGCAATCAGAAGTTGGCGACATATGTCTTTACTATATCGAACTT        75
TGGATATTATGGGAGCAGTGTGGCTTCATTTAAATACATTAGTGGAACAGTTATCTTTTTTACTGT    150
CCTCTTCTGCAGGAAACACTTGGTTTATGAGAGCCAAAAATGTCTTGCCTTTCTGATTCAAGGGTTACTGT  225
AAGCTGTCGGGGCCAATATCCACAATATTGCCCATCTGAAATCCATCTGTAGGGTGTGGCGCCCAAACGGGCTTT  300
CCATCCTCCTCCATTTTGAAGGAGGATCCACGATCTCCTGTTTCCACTATCCACTGTCACCGGTGCGGGAGCGAAGG  375
CAGGTGCGCGGCCATGGAGCGCGGTGAACGACGTTCGTGCGGCGTCTGGCCTGCTACACATACCAGGTGAG        450
              M  E  R  V  N  D  A  S  C  G  P  S  G  C  Y  T  Y  Q  V  S      20
CAGACACAGCACGGAGGAGATGCTGCACAACCTGAACCTGAACAACGGGCGCTTCTGCGACGTGCTCTT        525
   R  H  S  T  E  M  L  H  N  L  N  Q  R  N  G  R  F  C  D  V  L  L             45
GCGGGTAGGCGACGAGAGCTTCCCAGCGCACCGCGCCGTGCTGCCTGCAGCGAGTACTTTGAGTCGGTGTT        600
   R  V  G  D  E  S  F  P  A  H  R  A  V  L  A  A  C  S  E  Y  F  E  S  V  F     70
CAGCGCCCAGTTGGGCGACGGCGCGGAGCTGCGGAGGGTCCGGCTGATGTAGGGGCGACGGCAGCACCAGG        675
   S  A  Q  L  G  D  G  A  A  D  G  G  P  A  D  V  G  G  A  T  A  A  P  G        95
CGGCGGGGCCCGGCAGCTCCGGGGAGCTGGAGATGCACACTATCAGCTCCGAAGTATTTGGGGACATTCTGGACTT    750
   G  A  G  G  S  R  E  L  E  M  H  T  I  S  K  V  F  G  D  I  L  D  F          120
CGCCTACACTTCCCGCATCGTGTGCGCTTGCCTTGGAGAGCTTTCCCGAACTCATGACGGCGCCAAGTTCCTGCTGAT  825
   A  Y  T  S  R  I  V  R  L  E  S  F  P  E  L  M  T  A  A  K  F  L  L  M      145
GAGGTCGGTTATCGAGATCTGCCAGGAAGTCATCAAACAGTCAACAGATCCTGGTACCCCCTGCCCGCGC        900
   R  S  V  I  E  I  C  Q  E  V  I  K  Q  S  N  V  Q  I  L  V  P  P  A  R  A    170
CGATATAATGCTTTTTCGCCCCCCTCGGACTTGGGCTTCCCTTTGGACATGACCAACGGGGCAGCCTT        975
   D  I  M  L  F  R  P  P  G  T  S  D  L  G  F  P  L  D  M  T  N  G  A  A  L    195
GGCAGCCAACAGCAATGGCATGCCGGCAGCAGCTGGAGGAGGCCAGCTGGTGCTGCAGCCAT      1050
   A  A  N  S  N  G  I  A  G  S  M  Q  P  E  E  E  A  R  A  A  G  A  A  I      220
TGCAGGCCAAGCCTCTTTGCCTGTGTTACCTGGGGTTGACCCGCTTGCCCATGGTGGCTGGACCCCTATCCCCCCA    1125
   A  G  Q  A  S  L  P  V  L  P  G  V  D  R  L  P  M  V  A  G  P  L  S  P  Q    245
ACTGCTGACTTCCCCATTCCCCAGTGTGGCATGCCCCTGACTGCCAAGCGAGGCCGGGCCGCC      1200
   L  L  T  S  P  F  P  S  V  A  S  S  A  P  P  L  T  G  K  R  R  G  R  P      270
```

FIG. 9B

```
AAGGAAGGCCAACCTGCTGACTCAATGTTTGGTCCCAGGGGAGGCCTGAGGGAGGCAGGCATCCTTCCATGCGG      1275
 R  K  A  N  L  L  D  S  M  F  G  S  P  G  G  L  R  E  A  G  I  L  P  C  G        295
TCTATGTGGTAAGGTGTTCACTGATGCCAACCGGCTCCGGCAGGAGGCCCAGCACGGTGTCACCAGCCTCCA      1350
 L  C  G  K  V  F  T  D  A  N  R  L  R  Q  E  A  Q  H  G  V  T  S  L  Q         320
GCTGGGCTACACGGACCTTCCTCCTCCGAGGCTGGGTGAGAATGGGCTACCATCTGAAGACCCGACGGCCC      1425
 L  G  Y  I  D  L  P  P  P  R  L  G  E  N  G  L  P  I  S  E  D  P  D  G  P       345
CCGAAAGAGGAGCCGGACCAGGAAGCAGGTGGCTTGTGAGATCTGCGGCAAGATCTTCCGTGATGTGTATCATCT      1500
 R  K  R  S  R  T  R  K  Q  V  A  C  E  I  C  G  K  I  F  R  D  V  Y  H  L       370
TAACCGGCACAAGCTGTCCCACTCTGGGGAGAAGCCCTACTCCTGTGTGGGTTGCCTGTTCAAGAGAAA       1575
 N  R  H  K  L  S  H  S  G  E  K  P  Y  S  C  P  V  C  G  L  R  F  K  R  K       395
AGACCGCATGTCCTACCATGTCCGGTCCCATGATGGGTCCGTGGGCAAGCCTTACATCTGCCAGAGCTGTGGGAA     1650
 D  R  M  S  Y  H  V  R  S  H  D  G  S  V  G  K  P  Y  I  C  Q  S  C  G  K       420
AGGCTTCTCCAGGCCTGATCACTTGAACGACATATCAAGCAGTGCACACTTCTGAGCGGCCTCACAAGTGTCA    1725
 G  F  S  R  P  D  H  L  N  G  H  I  K  Q  V  H  T  S  E  R  P  H  K  C  Q       445
GACCTGCAATGCTTCTTTTGCCACCTGAGACCGTCTCCGCTCCACCTGCTGTCATGAAGACAAGGTGCCCTG     1800
 T  C  N  A  S  F  A  T  R  D  R  L  R  S  H  L  A  C  H  E  D  K  V  P  C       470
CCAGGTGTGTGGGAAGTACTTGCGGGCAGCAGATACACATGGACCACCTGAAGACACAGCGAGGGCCCAGCAA     1875
 Q  V  C  G  K  Y  L  R  A  A  Y  M  A  D  H  L  K  K  H  S  E  G  P  S  N       495
CTTCTGCAGTATCTGTAACCGAGAAGGCCAGAGAAATGCTCACATCAGGATCCGATTGAGAGCTCTGACTCCTATGG     1950
 F  C  S  I  C  N  R  E  G  Q  K  C  S  H  Q  D  P  I  E  S  S  D  S  Y  G       520
TGACCTCTCAGATGCCAGCGACCTGAAGACGCCAGAGAAGCAGAGTGCCAATGGCAGCTTCTCCTGCGACATGGC     2025
 D  L  S  D  A  S  D  L  K  T  P  E  K  Q  S  A  N  G  S  F  S  C  D  M  A       545
AGTCCCAAAAATGAATTGATGGGAGTCTGATGGGGAGAAGTACCCATGCCCTGAATGTGGGAGCTTCTTCCGCTC     2100
 V  P  K  N  M  E  S  D  G  E  R  K  Y  P  C  P  E  C  G  S  F  F  R  S        570
TAAGTCCTACTTGAACAAACACATCCAGAAGGTGCATGTCCGGGCTCTCGGGGACCTGGGCCC       2175
 K  S  Y  L  N  K  H  I  Q  K  V  H  V  R  A  L  G  P  L  G  D  L  G  P       595
TGCCCTTGGCTCACCTTTCTCTCCTCAGAGTCCTTTGGGTTTCAGATTGTTCAGTC      2250
 A  L  G  S  P  F  S  P  Q  Q  N  M  S  L  L  E  S  F  G  F  Q  I  V  Q  S       620
GGCATTTGCGTCATCTTTAGTAGATCCTGAGGTTGACCAGCCCATGGGGCCTGAAGGCCTGAAGGAAATGAGGCAGCTG     2325
```

FIG. 9C

```
  A   F   A   S   S   L   V   D   P   E   V   D   Q   Q   P   M   G   P   E   G   K   *                                    641
CTGTGTCCCCACGGAAACAACCATCTGGGACTGCTGTGAATGCGGAGGAAGTGATGTTTGGGT      2400
TCTGTAGCTGAGAGATTTTTATTCATTTTAACTGCCCCCACTCCTCTCCACCACCCATTC        2475
TCCCAATGGTCTTTAGAAATAGATTTCATCTGATATTCTGCAGAAATACAATCAATGGGA       2550
GCAGAAAACACTACATAGGCCTCCAAGCAAAACCAGTCCCAGTTTCTTTAATGGAAGCTGGAATTCCTGG  2625
TGCTCAATTCTTAGTGACCCCAAATCCTATACCCAAATCTATGATATTCTGGGACCCTCAGTGATTTGGTCCCCTC  2700
CCACTTCTCTAGTTCGTCGTCATCCTCCCCTTCCCCATATCCTTCCAAAGAACCACACTAGGGTCTCCACCTACTTATAC  2775
AATGCGGATGCCCAACTGTTTTTAAGGAAGCCAGAAGCATCCCATGACCCTGAGTGTCCTCCAAGAGCC      2850
CCCTGAGCTCAGCCCCTCAGCTCTGCCTGGAGGCCACCACCCCCAAATTTCAGTTCTTACGTGATTTAACCATTCACTGCT  2925
AGGACAAGCTCAGCTGTTGAGACACTGTCTCTAATTATTATTATTTTTAGGACCCAGTGTAGTGAATTGCTACTGA     3000
GTTGGGTTTTAATTCTCTAATTATTATTATTTTGTTATTATTTTAGGACCCAGTGTAGTAATTAGAGGTGTAGTATTAAACTTTGTTTAGA  3075
AAGCTATCCCAGTGATACAGAGACTCTTTGTAAACCGCAGTCACACATTAGGGTTAAAACTTTGTTTAGA      3150
TGTACCATAATTAACTTGGCTAGTTGATTGTTTGAAGTCTATGGAAGAAATAGTTTATGCAAAATTTTAAAAA       3225
TGCCAGTCTGGTCAGGGAAGTAGGGGGTTTCAATGCTGTTGGGAACCAGGAAGGTGGGACAGCCGGCAGGTAGGG     3300
ACATTGTGTACCTCAGTGTGTCACATGTGAGCAAGCCAGGTTGACCTTGTGATGTGAATTGATCTGATCAGAC    3375
TGTATTAAAAATGTTAGTACATTACTCT
```

Effects of cAMP on Localization of RIAZ

A Model for the Interaction of RIα with RIAZ

Expression of RIAZ in Human Breast Cancer Cell Lines

Expression of RIAZ in Human Cancer Cell Lines

Interaction of RIα with RIAZ

SEQUENCE LISTING

<160> NUMBER OF SEQ ID NOS: 18

<210> SEQ ID NO 1
<211> LENGTH: 131
<212> TYPE: PRT
<213> ORGANISM: Homo sapiens

<400> SEQUENCE: 1

His Ser Thr Glu Met Leu His Asn Leu Asn Gln Gln Arg Lys Asn Gly
1               5                   10                  15

Gly Arg Phe Cys Asp Val Leu Leu Arg Val Gly Asp Glu Ser Phe Pro
            20                  25                  30

Ala His Arg Ala Val Leu Ala Ala Cys Ser Glu Tyr Phe Glu Ser Val
        35                  40                  45

Phe Ser Ala Gln Leu Gly Asp Gly Gly Ala Ala Asp Gly Gly Pro Ala
    50                  55                  60

Asp Val Gly Gly Ala Thr Ala Ala Pro Gly Gly Gly Ala Gly Gly Ser
65                  70                  75                  80

Arg Glu Leu Glu Met His Thr Ile Ser Ser Lys Val Phe Gly Asp Ile
                85                  90                  95

Leu Asp Phe Ala Tyr Thr Ser Arg Ile Val Val Arg Leu Glu Ser Phe
            100                 105                 110

Pro Glu Leu Met Thr Ala Ala Lys Phe Leu Leu Met Arg Ser Val Ile
        115                 120                 125

Glu Ile Cys
    130

```
<210> SEQ ID NO 2
<211> LENGTH: 104
<212> TYPE: PRT
<213> ORGANISM: Homo sapiens

<400> SEQUENCE: 2

His Ser Gln His Val Leu Glu Gln Leu Asn Gln Gln Arg Leu Gly Leu
1               5                   10                  15

Leu Cys Asp Cys Thr Phe Val Val Asp Gly Val Asp His Phe Lys Ala
            20                  25                  30

His Lys Ala Val Leu Ala Ala Cys Ser Glu Tyr Phe Lys Met Leu Phe
        35                  40                  45

Val Asp Gln Lys Asp Val Val His Leu Asp Ile Val Ser Asn Ala Ala
    50                  55                  60

Gly Leu Gly Gln Met Leu Glu Phe Met Tyr Thr Ala Lys Leu Ser Leu
65                  70                  75                  80

Ser Pro Glu Asn Val Asp Val Leu Ala Val Ala Thr Phe Leu Gln
                85                  90                  95

Met Gln Asp Ile Ile Thr Ala Cys
            100

<210> SEQ ID NO 3
<211> LENGTH: 108
<212> TYPE: PRT
<213> ORGANISM: Homo sapiens

<400> SEQUENCE: 3

His Ala Ser Asp Val Leu Leu Asn Leu Asn Arg Leu Arg Ser Arg Asp
1               5                   10                  15

Ile Leu Thr Asp Val Val Ile Val Val Ser Arg Glu Gln Phe Arg Ala
            20                  25                  30

His Lys Thr Val Leu Met Ala Cys Ser Gly Leu Phe Tyr Ser Ile Phe
        35                  40                  45

Thr Asp Gln Leu Lys Cys Asn Leu Ser Val Ile Asn Leu Asp Pro Glu
    50                  55                  60

Ile Asn Pro Glu Gly Phe Cys Ile Leu Leu Asp Phe Met Tyr Thr Ser
65                  70                  75                  80

Arg Leu Asn Leu Arg Glu Gly Asn Ile Met Ala Val Met Ala Thr Ala
                85                  90                  95

Met Tyr Leu Gln Met Glu His Val Val Asp Thr Cys
            100                 105

<210> SEQ ID NO 4
<211> LENGTH: 105
<212> TYPE: PRT
<213> ORGANISM: Homo sapiens

<400> SEQUENCE: 4

His Pro Thr Gly Leu Leu Cys Lys Ala Asn Gln Met Arg Leu Ala Gly
1               5                   10                  15

Thr Leu Cys Asp Val Val Ile Met Val Asp Ser Gln Glu Phe His Ala
            20                  25                  30

His Arg Thr Val Leu Ala Cys Thr Ser Lys Met Phe Glu Ile Leu Phe
        35                  40                  45

His Arg Asn Ser Gln His Tyr Thr Leu Asp Phe Leu Ser Pro Lys Thr
    50                  55                  60

Phe Gln Gln Ile Leu Glu Tyr Ala Tyr Thr Thr Ala Thr Leu Gln Ala
65                  70                  75                  80
```

```
Lys Ala Glu Asp Leu Lys Asp Asp Leu Tyr Ala Ala Glu Ile Leu
                85                  90                  95

Glu Ile Glu Tyr Leu Glu Glu Gln Cys
            100                 105
```

<210> SEQ ID NO 5
<211> LENGTH: 107
<212> TYPE: PRT
<213> ORGANISM: Homo sapiens

<400> SEQUENCE: 5

```
His Lys Thr Leu Phe Leu Lys Thr Leu Asn Glu Gln Arg Leu Glu Gly
1               5                   10                  15

Glu Phe Cys Asp Ile Ala Ile Val Val Glu Asp Val Lys Phe Arg Ala
            20                  25                  30

His Arg Cys Val Leu Ala Ala Cys Ser Thr Tyr Phe Lys Lys Leu Phe
        35                  40                  45

Lys Lys Leu Glu Val Asp Ser Ser Val Ile Glu Ile Asp Phe Leu
    50                  55                  60

Arg Ser Asp Ile Phe Glu Glu Val Leu Asn Tyr Met Tyr Thr Ala Lys
65                  70                  75                  80

Ile Ser Val Lys Lys Glu Asp Val Asn Leu Met Met Ser Ser Gly Gln
                85                  90                  95

Ile Leu Gly Ile Arg Phe Leu Asp Lys Leu Cys
            100                 105
```

<210> SEQ ID NO 6
<211> LENGTH: 106
<212> TYPE: PRT
<213> ORGANISM: Homo sapiens

<400> SEQUENCE: 6

```
His Ser Leu Val Leu Leu Gln Gln Leu Asn Met Gln Arg Glu Phe Gly
1               5                   10                  15

Phe Leu Cys Asp Cys Thr Val Ala Ile Gly Asp Val Tyr Phe Lys Ala
            20                  25                  30

His Arg Ala Val Leu Ala Ala Phe Ser Asn Tyr Phe Lys Met Ile Phe
        35                  40                  45

Ile His Gln Thr Ser Glu Cys Ile Lys Ile Gln Pro Thr Asp Ile Gln
    50                  55                  60

Pro Asp Ile Phe Ser Tyr Leu Leu His Ile Met Tyr Thr Gly Lys Gly
65                  70                  75                  80

Pro Lys Gln Ile Val Asp His Ser Arg Leu Glu Glu Gly Ile Arg Phe
                85                  90                  95

Leu His Ala Asp Tyr Leu Ser His Ile Ala
            100                 105
```

<210> SEQ ID NO 7
<211> LENGTH: 108
<212> TYPE: PRT
<213> ORGANISM: Homo sapiens

<400> SEQUENCE: 7

```
His Ser Ser Glu Val Leu Cys Ser Leu Asn Glu Gln Arg His Asp Gly
1               5                   10                  15

Leu Leu Cys Asp Val Leu Leu Val Gln Glu Gln Glu Tyr Arg Thr
            20                  25                  30
```

His Arg Ser Val Leu Ala Ala Cys Ser Lys Tyr Phe Lys Lys Leu Phe
            35                  40                  45

Thr Ala Gly Thr Leu Ala Ser Gln Pro Tyr Val Tyr Glu Ile Asp Phe
 50                  55                  60

Val Gln Pro Glu Ala Leu Ala Ala Ile Leu Glu Phe Ala Tyr Thr Ser
 65                  70                  75                  80

Thr Leu Thr Ile Thr Ala Gly Asn Val Lys His Ile Leu Asn Ala Ala
            85                  90                  95

Arg Met Leu Glu Ile Gln Cys Ile Val Asn Val Cys
            100                 105

<210> SEQ ID NO 8
<211> LENGTH: 107
<212> TYPE: PRT
<213> ORGANISM: Homo sapiens

<400> SEQUENCE: 8

Gln Gln Gly Asp Val Val Leu Gln Lys Met Asn Leu Leu Arg Gln Gln
 1               5                  10                  15

Asn Leu Phe Cys Asp Val Ser Ile Tyr Ile Asn Asp Thr Glu Phe Gln
            20                  25                  30

Gly His Lys Val Ile Leu Ala Ala Cys Ser Thr Phe Met Arg Asp Gln
            35                  40                  45

Phe Leu Leu Thr Gln Ser Lys His Val Arg Ile Thr Ile Leu Gln Ser
 50                  55                  60

Ala Glu Val Gly Arg Lys Leu Lys Leu Leu Ser Cys Tyr Thr Gly Ala
 65                  70                  75                  80

Leu Glu Val Lys Arg Lys Glu Leu Leu Lys Tyr Leu Thr Ala Ala Ser
            85                  90                  95

Tyr Leu Gln Met Val His Ile Val Glu Lys Cys
            100                 105

<210> SEQ ID NO 9
<211> LENGTH: 24
<212> TYPE: PRT
<213> ORGANISM: Homo sapiens

<400> SEQUENCE: 9

Cys Gly Leu Cys Gly Lys Val Phe Thr Asp Ala Asn Arg Leu Arg Gln
 1               5                  10                  15

His Glu Ala Gln His Gly Val Thr
            20

<210> SEQ ID NO 10
<211> LENGTH: 24
<212> TYPE: PRT
<213> ORGANISM: Homo sapiens

<400> SEQUENCE: 10

Cys Glu Ile Cys Gly Lys Ile Phe Arg Asp Val Tyr His Leu Asn Arg
 1               5                  10                  15

His Lys Leu Ser His Ser Gly Glu
            20

<210> SEQ ID NO 11
<211> LENGTH: 24
<212> TYPE: PRT
<213> ORGANISM: Homo sapiens

<400> SEQUENCE: 11

-continued

Cys Pro Val Cys Gly Leu Arg Phe Lys Arg Lys Asp Arg Met Ser Tyr
1               5                   10                  15

His Val Arg Ser His Asp Gly Ser
            20

<210> SEQ ID NO 12
<211> LENGTH: 24
<212> TYPE: PRT
<213> ORGANISM: Homo sapiens

<400> SEQUENCE: 12

Cys Gln Ser Cys Gly Lys Gly Phe Ser Arg Pro Asp His Leu Asn Gly
1               5                   10                  15

His Ile Lys Gln Val His Thr Ser
            20

<210> SEQ ID NO 13
<211> LENGTH: 24
<212> TYPE: PRT
<213> ORGANISM: Homo sapiens

<400> SEQUENCE: 13

Cys Gln Thr Cys Asn Ala Ser Phe Ala Thr Arg Asp Arg Leu Arg Ser
1               5                   10                  15

His Leu Ala Cys His Glu Asp Lys
            20

<210> SEQ ID NO 14
<211> LENGTH: 24
<212> TYPE: PRT
<213> ORGANISM: Homo sapiens

<400> SEQUENCE: 14

Cys Gln Val Cys Gly Lys Tyr Leu Arg Ala Ala Tyr Met Ala Asp His
1               5                   10                  15

Leu Lys Lys His Ser Glu Gly Pro
            20

<210> SEQ ID NO 15
<211> LENGTH: 24
<212> TYPE: PRT
<213> ORGANISM: Homo sapiens

<400> SEQUENCE: 15

Cys Pro Glu Cys Gly Ser Phe Phe Arg Ser Lys Ser Tyr Leu Asn Lys
1               5                   10                  15

His Ile Gln Lys Val His Val Arg
            20

<210> SEQ ID NO 16
<211> LENGTH: 3402
<212> TYPE: DNA
<213> ORGANISM: Homo sapiens

<400> SEQUENCE: 16
gtcaaagtat gggattcact gcaatcagaa gttggcgaca tatgtatggg attctgtctt     60
tactatatcg aactttggat attatgggag cagtgtggct tcatttaaat acattagtgg    120
aacagttatc ttccacatct ttttactgt cctcttctgc agggaaacac ttggtttatg     180
agagccaaaa atgtcttgcc tttctgattc aagggttcaa ttgttaagct gtcggggcca    240

-continued

```
atatccacaa tattgcccat ctgaaatcca tctgtagggt gtggcgccca aacgggcttt      300
ccatcctcca ttttttgaagg aggatccacg atctcctgtt tccactatcc actgtcaccg     360
gtgcgggagc gaaggcaggt gcgcggcggc catggagcgg gtgaacgacg cttcgtgcgg     420
cccgtctggc tgctacacat accaggtgag cagacacagc acggagatgc tgcacaacct     480
gaaccagcag cgcaaaaacg gcgggcgctt ctgcgacgtg ctcttcgggt aggcgacgag     540
agcttcccag cgcaccgcgc cgtgctggcc gcctgcagcg agtactttga gtcggtgttc     600
agcgcccagt tgggcgacgg cggagctgcg gacggggggtc cggctgatgt aggggggcgcg    660 acggcagcac caggcggcgg ggccgggggc agccgggagc tggagatgca cactatcagc     720
tccaaggtat ttgggacat tctggacttc gcctacactt cccgcatcgt ggtgcgcttg      780
gagagctttc ccgaactcat gacggccgcc aagttcctgc tgatgaggtc ggttatcgag     840
atctgccagg aagtcatcaa acagtccaac gtacagatcc tggtaccccc tgcccgcgcc     900
gatataatgc ttttcgccc ccctgggacc tcggacttgg gcttcccttt ggacatgacc      960 aacgggcag ccttggcagc caacagcaat ggcatcgccg gcagcatgca gccagaggag    1020
gaggcagctc gggcggctgg tgcagccatt gcaggccaag cctctttgcc tgtgttacct     1080
ggggtggacc gcttgcccat ggtggctgga cccctatccc cccaactgct gacttcccca    1140
ttccccagtg tggcatccag tgcccctccc ctgactggca agcgaggccg gggccgccca    1200
aggaaggcca acctgctgga ctcaatgttt gggtccccag ggggcctgag ggaggcaggc    1260
atccttccat gcggtctatg tggtaaggtg ttcactgatg ccaaccggct ccggcagcac    1320
gaggcccagc acggtgtcac cagcctccag ctgggctaca tcgaccttcc tcctccgagg    1380
ctgggtgaga atgggctacc catctctgaa gaccccgacg gccccgaaa gaggagccgg     1440 accaggaagc aggtggcttg tgagatctgc ggcaagatct tccgtgatgt gtatcatctt    1500
aaccggcaca gctgtccca ctctgggggag aagccctact cctgccctgt gtgtgggttg     1560
cggttcaaga gaaaagaccg catgtcctac catgtgcggt cccatgatgg gtccgtgggc    1620
aagccttaca tctgccagag ctgtgggaaa ggcttctcca ggcctgatca cttgaacgga    1680
catatcaagc aggtgcacac ttctgagcgg cctcacaagt gtcagacctg caatgcttct    1740
tttgccaccc gagaccgtct gcgctcccac ctggcctgtc atgaagacaa ggtgccctgc    1800
caggtgtgtg ggaagtactt gcgggcagca tacatggcag accacctgaa gaagcacagc    1860
gaggggccca gcaacttctg cagtatctgt aaccgagaag gccagaaatg ctcacatcag    1920
gatccgattg agagctctga ctcctatggt gacctctcag atgccagcga cctgaagacg    1980
ccagagaagc agagtgccaa tggctctttc tcctgcgaca tggcagtccc caaaaacaaa    2040
atggagtctg atgggagaa gaagtaccca tgccctgaat gtgggagctt cttccgctct    2100
aagtcctact tgaacaaaca catccagaag gtgcatgtcc gggctctcgg ggcccccctg    2160
ggggacctgg gccctgccct tggctcacct ttctctcctc agcagaacat gtctctcctc    2220
gagtcctttg ggtttcagat tgttcagtcg gcatttgcgt catctttagt agatcctgag    2280
gttgaccagc agcccatggg gcctgaaggg aaatgaggca gctgctgtgt ccccacggaa    2340
acaaccatct ggggactgct gggaaatgct gtgaatgcgg agggaagtga tgtttgggtt    2400
ctgtagctga gagatttta ttcatttta actgcccccc aacccactc caactccttc       2460 tccaccaccc attctcccaa tggtctttag aaatagattt tcatctgata ttctgcagaa    2520
atatcaatga gacttggtat gggacagggg cagaaaacac tacataggcc tccaaggcaa    2580
aaccagtccc agtttctttta atgggaagaa gctggaattc ctggtgctca attcttagtg    2640
```

```
accccaatcc tatacccaaa tctatgatat tctgggacct cagtgatttt ggtcccctcc   2700
cacttctcta gttcgtcatc ctcccttccc atatccttca aaagaaccac actagggtct   2760
ccacctactt atacaatgcg gatgcccaac tgtttttaag gaagccagaa gcatcccatg   2820
gaccatgggg tgagtgtcct ccaagagccc cctgagctca gccctctgcc tggagggcac   2880 cagaccttc  tgagccctgc ttggaggcga gcattttcac tgctaggaca agctcagctg   2940
ttgaggacac ccccacccca aatttcagtt cttacgtgat tttaaccatt caacatgctg   3000
ttgggtttta attctctaat tattattatt attgttatta ttttttagga ccagttgtag   3060
tgaattgcta ctgaaagcta tcccaggtga tacagagctc tttgtaaacc gcagtcacac   3120
attagggtta gtattaaact tgtttagat  gtaccataat taacttggct agttgattgt   3180
ttgaagtcta tggaagaaat agttttatgc aaaattttaa aaaatgccag tctggtcagg   3240
gaagtagggg gtttcaatgc tgttgggaac caggaaggtg ggacagccgg caggtaggga   3300
cattgtgtac ctcagttgtg tcacatgtga gcaagcccag gttgaccttg tgatgtgaat   3360
tgatctgatc agactgtatt aaaaatgtta gtacattact ct                      3402
```

<210> SEQ ID NO 17
<211> LENGTH: 641
<212> TYPE: PRT
<213> ORGANISM: Homo sapiens

<400> SEQUENCE: 17

```
Met Glu Arg Val Asn Asp Ala Ser Cys Gly Pro Ser Gly Cys Tyr Thr
1               5                   10                  15

Tyr Gln Val Ser Arg His Ser Thr Glu Met Leu His Asn Leu Asn Gln
                20                  25                  30

Gln Arg Lys Asn Gly Gly Arg Phe Cys Asp Val Leu Leu Arg Val Gly
            35                  40                  45

Asp Glu Ser Phe Pro Ala His Arg Ala Val Leu Ala Ala Cys Ser Glu
        50                  55                  60

Tyr Phe Glu Ser Val Phe Ser Ala Gln Leu Gly Asp Gly Gly Ala Ala
65                  70                  75                  80

Asp Gly Gly Pro Ala Asp Val Gly Gly Ala Thr Ala Ala Pro Gly Gly
                85                  90                  95

Gly Ala Gly Gly Ser Arg Glu Leu Glu Met His Thr Ile Ser Ser Lys
            100                 105                 110

Val Phe Gly Asp Ile Leu Asp Phe Ala Tyr Thr Ser Arg Ile Val Val
        115                 120                 125

Arg Leu Glu Ser Phe Pro Glu Leu Met Thr Ala Ala Lys Phe Leu Leu
    130                 135                 140

Met Arg Ser Val Ile Glu Ile Cys Gln Glu Val Ile Lys Gln Ser Asn
145                 150                 155                 160

Val Gln Ile Leu Val Pro Ala Arg Ala Asp Ile Met Leu Phe Arg
                165                 170                 175

Pro Pro Gly Thr Ser Asp Leu Gly Phe Pro Leu Asp Met Thr Asn Gly
            180                 185                 190

Ala Ala Leu Ala Ala Asn Ser Asn Gly Ile Ala Gly Ser Met Gln Pro
        195                 200                 205

Glu Glu Glu Ala Ala Arg Ala Ala Gly Ala Ala Ile Ala Gly Gln Ala
    210                 215                 220

Ser Leu Pro Val Leu Pro Gly Val Asp Arg Leu Pro Met Val Ala Gly
225                 230                 235                 240
```

-continued

```
Pro Leu Ser Pro Gln Leu Leu Thr Ser Pro Phe Pro Ser Val Ala Ser
            245                 250                 255

Ser Ala Pro Pro Leu Thr Gly Lys Arg Gly Arg Gly Arg Pro Arg Lys
        260                 265                 270

Ala Asn Leu Leu Asp Ser Met Phe Gly Ser Pro Gly Gly Leu Arg Glu
    275                 280                 285

Ala Gly Ile Leu Pro Cys Gly Leu Cys Gly Lys Val Phe Thr Asp Ala
290                 295                 300

Asn Arg Leu Arg Gln His Glu Ala Gln His Gly Val Thr Ser Leu Gln
305                 310                 315                 320

Leu Gly Tyr Ile Asp Leu Pro Pro Arg Leu Gly Glu Asn Gly Leu
                325                 330                 335

Pro Ile Ser Glu Asp Pro Asp Gly Pro Arg Lys Arg Ser Arg Thr Arg
            340                 345                 350

Lys Gln Val Ala Cys Glu Ile Cys Gly Lys Ile Phe Arg Asp Val Tyr
        355                 360                 365

His Leu Asn Arg His Lys Leu Ser His Ser Gly Glu Lys Pro Tyr Ser
    370                 375                 380

Cys Pro Val Cys Gly Leu Arg Phe Lys Arg Lys Asp Arg Met Ser Tyr
385                 390                 395                 400

His Val Arg Ser His Asp Gly Ser Val Gly Lys Pro Tyr Ile Cys Gln
                405                 410                 415

Ser Cys Gly Lys Gly Phe Ser Arg Pro Asp His Leu Asn Gly His Ile
            420                 425                 430

Lys Gln Val His Thr Ser Glu Arg Pro His Lys Cys Gln Thr Cys Asn
        435                 440                 445

Ala Ser Phe Ala Thr Arg Asp Arg Leu Arg Ser His Leu Ala Cys His
    450                 455                 460

Glu Asp Lys Val Pro Cys Gln Val Cys Gly Lys Tyr Leu Arg Ala Ala
465                 470                 475                 480

Tyr Met Ala Asp His Leu Lys Lys His Ser Glu Gly Pro Ser Asn Phe
                485                 490                 495

Cys Ser Ile Cys Asn Arg Glu Gly Gln Lys Cys Ser His Gln Asp Pro
            500                 505                 510

Ile Glu Ser Ser Asp Ser Tyr Gly Asp Leu Ser Asp Ala Ser Asp Leu
        515                 520                 525

Lys Thr Pro Glu Lys Gln Ser Ala Asn Gly Ser Phe Ser Cys Asp Met
530                 535                 540

Ala Val Pro Lys Asn Lys Met Glu Ser Asp Gly Glu Lys Lys Tyr Pro
545                 550                 555                 560

Cys Pro Glu Cys Gly Ser Phe Phe Arg Ser Lys Ser Tyr Leu Asn Lys
                565                 570                 575

His Ile Gln Lys Val His Val Arg Ala Leu Gly Pro Leu Gly Asp
            580                 585                 590

Leu Gly Pro Ala Leu Gly Ser Pro Phe Ser Pro Gln Gln Asn Met Ser
        595                 600                 605

Leu Leu Glu Ser Phe Gly Phe Gln Ile Val Gln Ser Ala Phe Ala Ser
    610                 615                 620

Ser Leu Val Asp Pro Glu Val Asp Gln Gln Pro Met Gly Pro Glu Gly
625                 630                 635                 640

Lys
```

```
-continued

<210> SEQ ID NO 18
<211> LENGTH: 24
<212> TYPE: PRT
<213> ORGANISM: artificial sequence
<220> FEATURE:
<223> OTHER INFORMATION: consensus sequence
<220> FEATURE:
<221> NAME/KEY: misc_feature
<222> LOCATION: (2)..(3)
<223> OTHER INFORMATION: X represents any amino acid.
<220> FEATURE:
<221> NAME/KEY: misc_feature
<222> LOCATION: (5)..(7)
<223> OTHER INFORMATION: X represents any amino acid.
<220> FEATURE:
<221> NAME/KEY: misc_feature
<222> LOCATION: (9)..(13)
<223> OTHER INFORMATION: X represents any amino acid.
<220> FEATURE:
<221> NAME/KEY: misc_feature
<222> LOCATION: (15)..(16)
<223> OTHER INFORMATION: X represents any amino acid.
<220> FEATURE:
<221> NAME/KEY: misc_feature
<222> LOCATION: (18)..(20)
<223> OTHER INFORMATION: X represents any amino acid.
<220> FEATURE:
<221> NAME/KEY: misc_feature
<222> LOCATION: (22)..(24)
<223> OTHER INFORMATION: X represents any amino acid.

<400> SEQUENCE: 18

Cys Xaa Xaa Cys Xaa Xaa Xaa Phe Xaa Xaa Xaa Xaa Xaa Leu Xaa Xaa
1               5                   10                  15

His Xaa Xaa Xaa His Xaa Xaa Xaa
            20
```

NUCLEIC ACID AND PROTEIN EXPRESSION THEREBY AND THEIR INVOLVEMENT IN STRESS

CROSS-REFERENCE TO RELATED APPLICATIONS

The present application is a continuation application of PCT/US00/33438, filed Dec. 7, 2000, which claims priority to provisional application Ser. No. 60/169,418, filed Dec. 7, 1999, the disclosures of which are incorporated by reference herein in their entireties. Applicants claim the benefits of this application under 35 U.S.C. §119 (a)–(d) and 35 U.S.C. §119 (e).

BACKGROUND OF THE INVENTION

Since its discovery, the only known mechanism of signaling for cAMP involves its binding to the regulatory (R) subunit of the cAMP-dependent protein kinase (PKA) that leads to the dissociation of the holoenzyme and activation of the catalytic (C) subunit kinase. There have been speculations that the R subunit of PKA may have other functions in addition to inhibiting the C subunit kinase activity. However, evidence linking a function to the R subunit has been elusive.

Signal Transduction Pathway of cAMP

The cAMP-signal-transduction-pathway-mediated phosphorylation can be elicited by various physiological ligands in cells and is critically involved in the regulation of metabolisms, cell growth and differentiation, apoptosis, and gene expression. The PKA holoenzyme is composed of two genetically distinct subunits, catalytic (C) and regulatory (R), forming a tetrameric holoenzyme $R_2C_2$ which, in the presence of cAMP, dissociates into an $R_2(cAMP)_4$ dimer and two free catalytically active C subunits. There are two major R subunit isoforms which are further distinguished as RIα and RIβ, and RIIα and RIIβ, and three isoforms of the C subunit, Cα, Cβ, and Cγ. Defects in the formation or action of cAMP may cause cellular transformation. (Cho-Chung, Y. S. (1990) Cancer Res., 50:7093–7100; Gottesman, M. M., and Fleischmann, R. D. (1986) Cancer Surveys, 5:291–308). Furthermore, differential expression of RI and RII has been correlated with cell differentiation and neoplastic transformation. In fact, while RI is preferentially expressed in transformed cells, expression of RII is increased in terminally differentiated tissues. (Cho-Chung, Y. S. (1990) Cancer Res. 50:7093–7100).

Mechanisms of cAMP Signaling

For approximately forty years, the R subunit has been the only known receptor for cAMP in cells and cAMP binding to the holoenzyme has been the accepted mechanism that regulates PKA activity. However, this dogma of cAMP signaling is being rewritten to accommodate some recent discoveries that implicate the existence of alternative mechanisms for the cAMP messenger system (FIG. 1). The first hint of a novel alternative mechanism for cAMP signaling came from studies that show the direct interaction of cAMP with some ion channels in the central nervous system (Liu, F. C., et al (1995) J. Neurosci, 15:2367–2384; Zufall, F. et al, (1997) Curr. Opin. Neurobiol., 7:404–412; Santoro, B. et al (1998) Cell, 93:717–729)., suggesting that there are receptors, other than the R subunit, that mediate the action of cAMP. This was followed by a study that demonstrated that the C subunit can be activated in a cAMP- and R subunit-independent manner, in a ternary complex of $NF_\kappa B$-$I_\kappa B$-C subunit (Zhong, H. et al (1997) Cell 89:413–424). Degradation of $I_\kappa B$ following the exposure to inducers of $NF_\kappa B$ leads to the activation of the C subunit in a cAMP-independent manner and subsequent phosphorylation of $NF_\kappa B$. Recently, a novel family of cAMP-binding guanine nucleotide exchange factors was identified which can selectively activate the Ras superfamily of guanine nucleotide binding protein Rap 1 in a cAMP-dependent but PKA independent manner (De Rooij, J. et al (1998) Nature 396:474–477; Kawasaki, H. et al (1998) Science 282:2275–2279).

Functions for the Regulatory Subunit

There has also been speculation that the R subunit could act through mechanisms other than C subunit activation. One possibility is that R subunit containing bound cAMP has functions independent of its interaction with the C subunit. For example, cAMP-bound RII subunit complex but not the C subunit nor the protein kinase holoenzyme inhibits phosphorylase phosphatase activity, leading to prolongation of the glycogen breakdown cascade (Gergley, P. and Bot, G. (1997) FEBS Letters 82:269–272). Gergley et al. suggested that the inhibition of phosphorylase phosphatase activity by the R subunit was through a substrate-directed mechanism perhaps through conformational modification of phosphorylase a. The RII subunit also inhibits the activity of a purified high molecular weight phosphoprotein phosphatase in a cAMP-dependent manner and that the inhibited species is an RII-cAMP-phosphatase complex (Khatra, B. S. et al (1985) Biophy. Res. Comm. 130:567–572). By inhibiting phosphatase activity, the R subunit may magnify the effect of C subunit phosphorylation. In addition, the RII subunit associates with numerous binding proteins known as the A-kinase anchoring proteins (AKAPs), which serve to localize the inactive PKA holoenzyme in specific subcellular compartments (Dell'Acqua, M. L. and Scott, J. D. (1997) J. Biol. Chem. 272:12881–12884; Pawson, T. and Scott, J. D. (1997) Science 278:2075–2080). These studies together suggest that the R subunit may interact with other proteins in addition to the C subunit.

Recently, it was also found that RIα interacts with the ligand-activated epidermal growth factor receptor (EGFR) complex (Tortora, G. et al (1997) Oncogene 14:923–928). Coimmunoprecipitation with an anti-RIα antibody demonstrated the binding of RIα to the SH3 domains of the Grb2 adaptor protein, allowing the localization of the type I PKA to the activated EGFR (Tortora, G. et al (1997) Oncogene 14:923–928). Using affinity chromatography and immunoprecipitation, another study provided evidence for a direct interaction between RIα and the $p34^{cdc2}$ protein kinase cell cycle regulator, presenting the possibility of interdependent functioning of these two pathways in the regulation of cell division (Toumier, S. et al (1991) J. Biol. Chem. 266: 19018–19022).

The role of cAMP in cell growth has been widely studied (Cho-Chung, Y. S. (1990) Cancer Res. 50:7093–7100). In a large number of human cancer cell lines, RI isoform is the only R subunit of PKA detected. In human cancer specimens, the predominant expression of type I PKA or the RI subunit is consistently observed. It has been shown that overexpression of RIα in Chinese hamster ovary (CHO) cells rendered growth advantages in monolayer and soft agar conditions, whereas overexpression of the C subunit did not produce such consequences (Tortora, G. et al (1994) Int. J. Cancer 59:712–716). Similarly, overexpression of RIα, but not the C subunit, in MCF-10A cells conferred the ability to grow in serum and growth-factor free conditions (Tortora, G. et al (1994) Oncogene 9:3233–3240). It is apparent from these studies that the role of cAMP in cell growth cannot be explained by changes in the kinase activity and further raises the possibility that the R subunit or an unidentified cAMP receptor molecule may mediate the effects of cAMP.

Cyclic AMP Signaling and Gene Regulation

In eukaryotes, transcriptional regulation by the cAMP signaling pathway is mediated by a family of cAMP-responsive nuclear transcription factors (Lalli et al. (1994) J. Biol. Chem. 269:17359–17362; Daniel et al. (1998) Aannu. Rev. Nutr. 18:353–383). These factors may act as either activators or repressors and they contain signature basic domain/leucine zipper motifs and bind as dimers to cAMP-responsive elements (CRE). The consensus CRE has the nucleotide sequence TGACGTCA as found in many promoters of cAMP regulated genes. The CRE-binding proteins (CREB) and modulators (CREM) are regulated by phosphorylation by PKA. Binding of cAMP to the R subunits releases the C subunits, thus enabling a fraction of the C subunit to enter the nucleus and phosphorylate its target proteins which include a large number of the CREB and CREM family of proteins. CREB and CREM belong to a group of transcription factors that contain basic region leucine zippers, bZIP, which is central for DNA recognition and binding, and protein-protein interaction (homo- and heterodimerization) among family members. In addition, a kinase-inducible domain (KID) also known as the phosphorylation box (P-box), contains potential phosphorylation sites for PKA and several different kinases that are critical for the transactivation properties of CREB and CREM. The phosphorylation of CREB/CREM within the KID domain induces their association with transcriptional coactivators, such as the nuclear factor CBP (CREB binding protein) or its closely related but distinct nuclear factor p300.

Several other transcription factors are also regulated by and are responsive to the activation of the cAMP signaling pathway, including the activating transcription factor-1 (ATF-1), NFκB, AP-2, and some nuclear receptors (Daniel et al. Supra.). Of specific interest is NFκB, which is a cytoplasmically localized transcription factor and may be directly controlled by cAMP (Naumann et al. (1994) EMBO J 13:4597–4607; Neumann (1995) EMBO J 14:1991–2004). Elevation of cAMP levels can either activate or inhibit NFκB regulated gene expression. Furthermore, there is also evidence that signals that cause degradation of IκB allows the complexed C subunit to phosphorylate NFκB and further activates NFκB and its translocation into the nucleus (Zhong et al. (1997) Cell 89:413–424). As alluded to above, the RIIβ subunit can also act directly as a transcription activator of CRE-regulated gene expression.

PKA Signaling in Yeast

In the yeast S. cerevisiae, PKA activity has been implicated in numerous cellular processes, including growth, carbon storage, response to stress and differentiation (Cameron et al. (1988) Cell 53:555–566; Broach et al (1990) Adv. Cancer Res. 54:79–138; Gimeno et al. (1992) Cell 68:1077–1090). In contrast to mammalian cells, the R subunit of PKA in yeast is encoded by the single BCY1 gene and the C subunits are encoded by three TPK genes (termed TPK1, TPK2, and TPK3) (Matsumato et al (1985) Yeast 1:15–24; Cannon et al. (1987) Mol. Cell Biol. 7:2653–2663; Toda et al (1987) Mol. Cell Biol 7:1371–1377; Toda et al. (1987) Cell 50:277–287). In S. cerevisiae, exposure to mild stress leads to development of tolerance against higher doses of the same stress and also cross tolerance to stress caused by other agents. Stress initiates expression of genes encoding proteins with stress-protective functions. Transcriptional control by multiple stress conditions is mediated by the stress response element (STRE) (Moskovina et al. (1999) Mol. Microbiol. 32:1263–1272). S. Cerevisiae PKA acts as a powerful repressor of STRE-mediated transcription (Moskovina, Supra.; Smith et al. (1998) EMBO J. 17:3556–3564). It appears to provide a link between positive control of cell growth and negative control of stress response.

Although the precise mechanism of the general stress response pathway has not been elucidated, recent studies have implicated the related zinc finger transcription factors Msn2p and Msn4p in this process (40–42). Strains lacking MSN2 and MSN4 are sensitive to various forms of stress and fail to accumulate stress-regulated messages following heat and osmotic stress, as well as nutrient starvation and DNA damage. Furthermore, it has been shown that Msn2p and Msn4p can recognize and bind STREs in vitro (40,41). These proteins appear to be functionally redundant, as double but not single mutants exhibit pleiotropic stress sensitivity. Msn2p seems to have a more pronounced role, but full stress-induced expression of STRE-regulated genes is dependent on the presence of both Msn2p and Msn4p. Msn2p/Msn4p relocate from the cytoplasm and accumulate in the nucleus under stress conditions. Nuclear localization of Msn2p/Msn4p is inversely correlated with cAMP levels and PKA activity (43). It is intriguing that the response to multiple stresses and to PKA activity can be mediated by only one type of transcription factor. In mammalian cells, pathways linking transcriptional response to multistress mediated by factors shutting between cytoplasm and nucleus, have not been explored. The presence of a comparable cAMP-regulated multistress response pathway and the Msn2p/Msn4p shuttling factors in higher eukaryotes remains an exciting possibility.

Cis Platin Resistance and Regulation of DNA Repair in cAMP-Dependent Protein Kinase Mutants It has been demonstrated that the mouse Y1 adrenocortical carcinoma and CHO cells harboring defective RIα subunits of PKA, with decreased kinase activity, exhibit increased resistance to cisplatin (Liu, B. et al (1996) Cell growth and Differ. 7:1105–1112). In contrast, C subunit mutants also with diminished response to cAMP and decreased kinase activity, have similar sensitivity to cisplatin as wild-type cells, suggesting that the R subunit may confer resistance independent of the C subunit kinase activity. Moreover, wild-type cells transfected with a mouse dominant mutant RIα cDNA are also more resistant to cisplatin than wild-type cells. In addition, increased nuclear protein binding to cisplatin-damaged DNA was observed with nuclear extracts from RIα mutant compared to wild-type and C subunit mutants. A host cell reactivation assay also indicate that RIα mutant repairs and reactivates a cisplatin damaged reporter plasmid more efficiently than wild-type cells and the C subunit mutant. These results suggest that alteration specifically in the RIα subunit, but not the C subunit nor the kinase activity, confers cellular resistance to cisplatin. We further speculate that the RIα subunit may have other functions and regulate drug resistance.

Regulation of P-Glycoprotein Expression in cAMP-Dependent Protein Kinase Mutants Additional evidence supporting a function for R subunit in drug resistanceis stemmed from studies on multidrug resistance (Cvijic, M. E. and Chin, K. V. (1997) Cell growth and Diff. 8:1243–1247). It has been shown that the RIα subunit mutants of CHO cells exhibited increased sensitivity to chemotherapeutic agents that are substrates for the multidrug transporter or P-glycoprotein (Abraham, I. et al (1987) Mol. Cell. Bio. 7:3098–3106; Abraham, I. et al (1990) Exp. Cell. Res. 189:133–141; Chin, K. V. et al (1992) J. Cell. Physiol. 152:87–94). The alteration in drug sensitivity in the RIα mutants resulted from a reduced expression of the multidrug resistance (mdr) gene. In the current study, we further examined the drug sensitivity and iP-glycoprotein levels in a series of C subunit mutants of the CHO cells. Our results revealed that these mutants exhibit similar sensitivity as wild-type cells to adriamycin, taxol and colchicine. Furthermore, no changes in P-glycoprotein expression was observed with these C subunit mutants compared to the wild-type cells. These results suggest that the decreased mdr gene expression in the RIα subunit mutants may be a result of the mutation and altered function of the RIα gene rather than alteration of the kinase activity, further supporting that RIα may regulate drug resistance independent of the kinase.

Effects of RIα Overexpression on Cisplatin Sensitivity in Carcinoma Cells

RIα has been overexpressed in the human ovarian carcinoma A2780 cells to demonstrate that modulating RIα levels can influence cellular sensitivity to cisplatin (Cvijic, M. E. and Chin, K. V. (1998) BBRC 249–723–727). Retroviralinfected A2780 cells overexpressing wild-type RIα cDNA displayed a 4- to 8-fold greater sensitivity to cisplatin as compared with parental cells. Overexpression of RIα in the CP70 cisplatin-resistant derivative of A2780 also increased the sensitivity of these cells to cisplatin. Therefore, enhanced expression of the RIα subunit of PKA sensitizes cells to the cytotoxic effects of this DNA-damaging agent. These data suggest that RIα may act directly, independent of the C subunit, to influence cellular sensitivity to cisplatin. Therefore, modulation of RIα expression or its functional status by pharmacological agents may be clinically useful in reverse cisplatin resistance in cancer.

Cisplatin Sensitivity of PKA Mutants in *S. Cerevisiae*

The role of PKA in cellular sensitivity to cisplatin was evaluated in a series of PKA mutants of *Saccharomyces cerevisiae* (Cvijic, M. E. et al (1998) Anticancer Res. 18:3187–3192). Mutants with decreased kinase activity resulting from a srv2 mutation showed no alterations in cisplatin sensitivity. Complementation of TPK1, the yeast C subunit of PKA, in a mutant strain containing tpk1 and also tpk2 and tpk3 deletions did not significantly alter its sensitivity to cisplatin. Yeast transformants containing increased kinase activity resulting from overexpression of RAS2$^{Val19}$ or TPK1 and yeast strains having increased kinase activities due to mutations in the R subunit, BCY1, gene also did not show alterations in their sensitivity to cisplatin. Therefore, these results unambiguously demonstrate that changes in PKA activity owing to either mutations in the C subunit or indirectly through alterations in other molecules of the cAMP signaling pathway, have no effect on cisplatin sensitivity in *S. cerevisiae*.

PKA R Subunit Interacts with Cytochrome Oxidase Subunit Vb

To gain further understanding of the function of RIα, Yang et al performed the yeast two-hybrid interaction cloning experiments and showed that the RIα subunit associates with the cytochrome c oxidase subunit Vb (CoxVb) (Yang, W. L. et al (1998) Biochemistry 37:14175–14180). The mammalian cytochrome c oxidase, composed of 13 polypeptide subunits, is the terminal enzyme complex of the electron transfer chain that oxidizes cytochrome c and transfers electrons to molecular oxygen to form water and the synthesis of ATP. We show further that CoxVb interacts with the GST-RIα fusion protein and also coimmunoprecipitates RIα in cell extracts. Binding of CoxVb to RIα can be dissociated with cAMP. Treatment with cAMP-elevating agents inhibits cytochrome c oxidase activity in CHO cells with a concomitant decrease in cytochrome c levels in the mitochondria and an increase in its release into the cytosol. Furthermore, mutant cells harboring a defective RIα show increased cytochrome c oxidase activity and also constitutively lower levels of cytochrome c in comparison to either the wild-type cells or the C subunit mutant. These results suggest a novel mechanism of cAMP signaling through the interaction of RIα with CoxVb thereby regulating cytochrome c oxidase activity as well as the release of cytochrome.

SUMMARY OF THE INVENTION

In its broadest aspect, the present invention relates to a factor determined herein to play a role in the host response to stress, which comprises a protein defined herein as RIα Interacting Zinc Finger Protein (RIAZ). The invention extends to the protein, active fragments, analogs and mimics thereof, and to the corresponding nucleic acid encoding the protein, conserved variants, and fragments thereof, both the protein and nucleic acid sequences set forth in FIG. 9 hereof. The invention extends to diagnostic and therapeutic applications for both the nucleic acids and the proteins, including drug discovery assays, and methods of treatment including modulation of chemosensitivity, and progression of neoplasm involving such techniques as gene therapy, among others.

It is an object of the invention to provide a zinc finger binding protein.

It is a further object of the invention to provide a gene encoding the zinc finger binding protein.

It is a further object of the invention to provide a method of controlling drug resistance in cancer cells.

These and other objects and advantages of the current invention will become apparent to those skilled in the art from the accompanying description of the current invention which proceeds with reference to the following drawing figures.

BRIEF DESCRIPTION OF THE DRAWINGS

FIG. 3. Interaction of RIAZ with RIα. RIα cDNA was cloned into the GAL4 DNA binding domain vector pAS2-1 as bait to screen a human liver two-hybrid cDNA library. Test crosses are shown for yeast matings (MATa×MATα, left panel) in which association of RIα with expressed proteins resulted in the expression of the β-galactosidase reporter (blue colonies, right panel). pACT2-A14 is the yeast two-hybrid clone containing the C-terminus of RIAZ. Interaction of RIα with itself (dimerization) was used as positive control, and SNF1, the snf1 protein kinase, was the negative control where neither RIα nor pACT2-A14 (RIAZ) showed interaction.

Figure 4A:
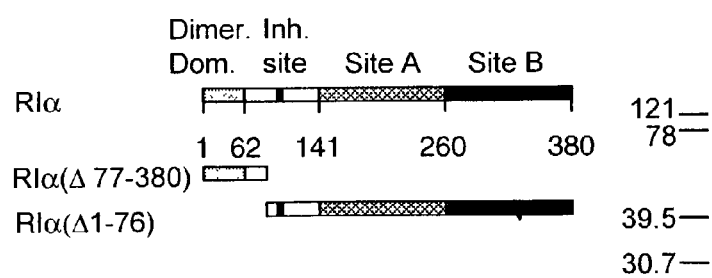
Figure 4B:
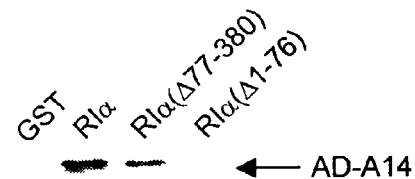

FIGS. 4A and 4B. Deletion analysis of RIα and its interaction with RIAZ.

FIG. 4A. The amino terminal deletion mutant GST-RIα (Δ1–76) and the carboxyl terminal deletion mutant GST-RIα(Δ77–380) were expressed in E. coli. The N-terminal dimerization domain (Dimer. Dom.), inhibitory site (Inh. site), and the two cAMP binding domains are indicated on the wild-type RIα.

FIG. 4B. Bacterial lysates containing the expressed proteins were incubated with glutathione resin to immobilize the GST-RIα deletion mutants followed by incubation with yeast protein lysates containing GAD-A14. The associated proteins were analyzed by SDS-PAGE and Western blot using anti-GAD antibody. Lane 1, GST; 2, GST-RIα; 3, GST-RIα(Δ77–380); 4, GST-RIα(Δ1–76). Lower panel is Ponceau S stained nitrocellulose membrane to monitor loading.

Figure 5:
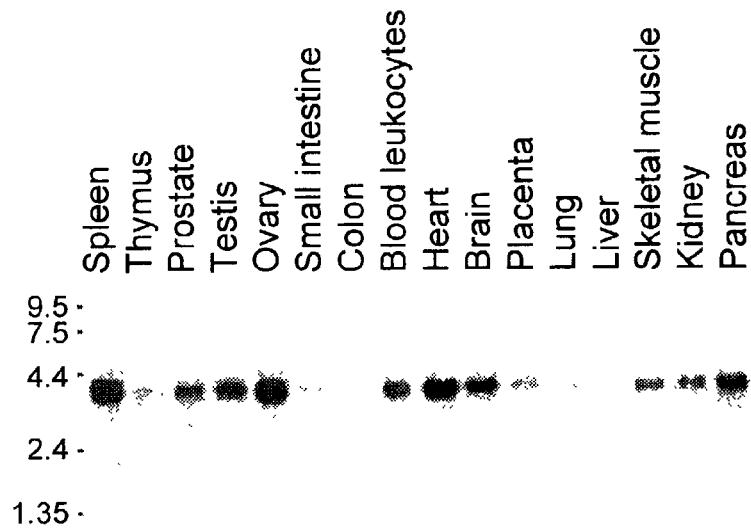

FIG. 5. Differential expression of RIAZ in human adult tissues by Northern hybridization analysis. Poly(A)+RNAs from various normal human tissues were hybridized with a probe derived from the 3' end of RIAZ cDNA encompassing nucleotides 2616 to 3403.

Figures 6A, 6C:
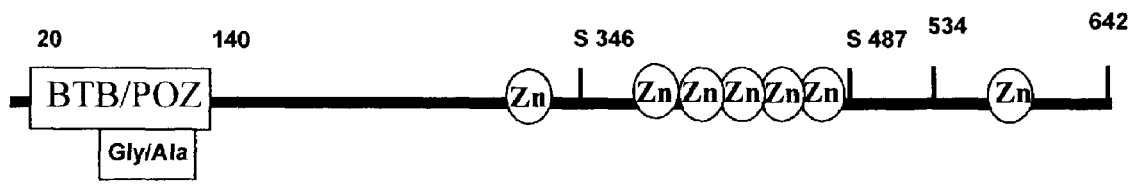

FIGS. 6A through 6C. Structure of RIAZ.

FIG. 6A. Schematic representation of RIAZ.

FIG. 6B. Amino Acid sequences of the structurally conserved BTB-POZ domain of RIAZ and other members of this family of BTB-POZ zinc finger transcription factors. The sequences depicted in FIG. 6B are SEQ ID NOS. 1–8 (RIAZ, MIZ-1, BCL-6, PLZF, ZF5, KUP, APM-1, and ZID respectively).

FIG. 6C. Amino acid sequences of the $C_2H_2$ type zinc finger motifs in RIAZ. The underlined amino acids represent the aligned $C_2H_2$ type zinc finger consensus in RIAZ. The sequences depicted in FIG. 6C are SEQ ID NOS: 18 and 9–15 (consensus, Finger, 1, Finger 2, Finger 3, Finger 4, Finger 5, Finger 6, and Finger 7 respectively).

Figure 7:
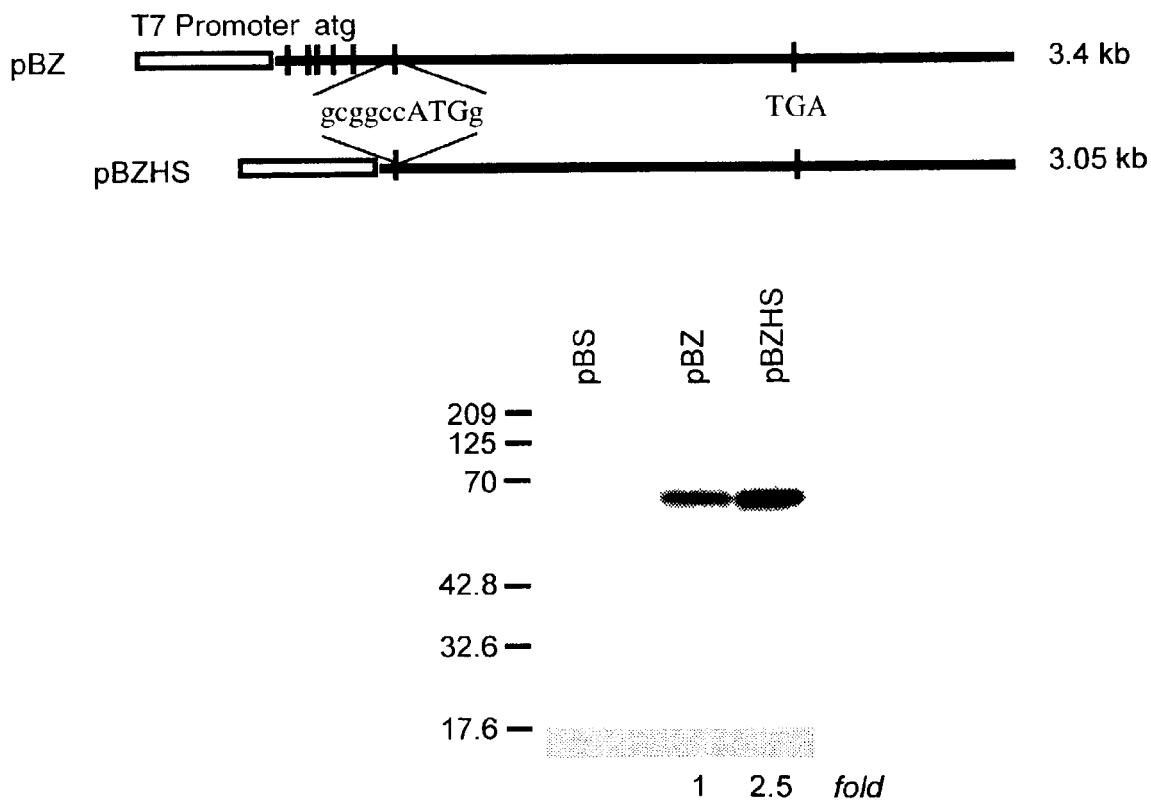

FIG. 7. In vitro-translated product of RIAZ. Schematic representation of RIAZ cDNA cloned into pBluescript II SK(-). The in vitro-tranlated products of RIAZ are labeled with [$^{35}$S]methionine, separated by SDS-PAGE, and exposed to X-ray film. Lane 1, pBluescript II SK(-); lane 2, pBZ, full length RIAZ cDNA; lane 3, pBZHS, approximately 350 bp 5' deletion of a cluster of upstream ATG from the putative open reading frame.

Figure 8:
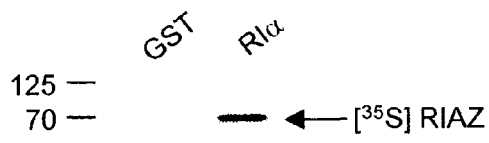

FIG. 8. Binding of in-vitro translated RIAZ protein to RIα. GST and GST-RIα proteins were immobilized on glutathione resins and then incubated with [$^{35}$S]methinine labeled RIAZ. The complexes were thoroughly washed and eluted in gel-loading buffer, separated by SDS-PAGE, and exposed to X-ray film.

FIG. 9 (Parts 1 and 2). A full length sequence of the gene encoding RIAZ. The sequences depicted in FIG. 9 are SEQ ID NO: 16 (DNA) and SEQ ID NO: 17 (amino acid).

Figure 10:
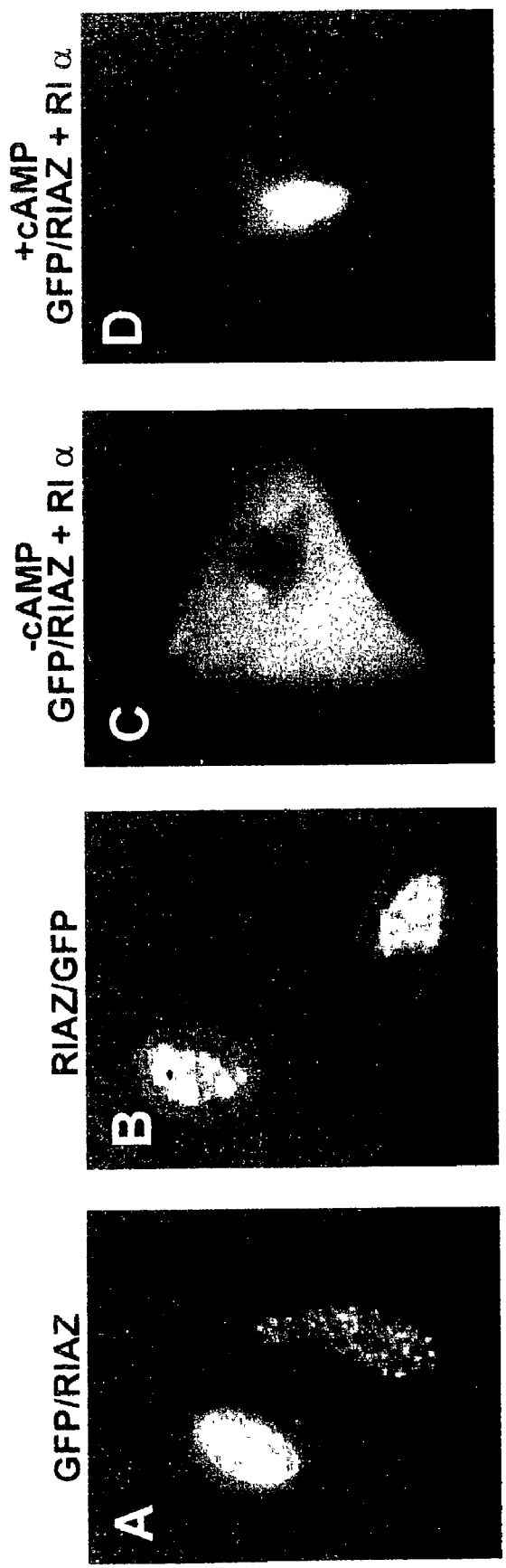

FIG. 10 depicts the effect of RIα and cAMP on localization of RIAZ. GJP fusions at the N-terminus (GFP/RIAZ) and the C-terminus (RIAZ/GFP) were generated. Panel A shows GFP/RIAZ nuclear expression as visualized by GFP. Panel B shows RIAZ/GFP nuclear expression as visualized by GFP. Panel C shows cytoplasmic localization of GFP/RIAZ on co-transfection with RIα, in the absence of cAMP. Localization of GFP/RIAZ on co-transfection with RIα is redistributed to the nucleus on addition of cAMP(Panel D). In more detail, nuclear localization of RIAZ and regulation of its localization by RIα in the presence or absence of cAMP was performed as follows: (A,B) HTB-46 cells were plated the night before and then transfected with GFP/RIAZ the following day. Localization of RIAZ was visualized 24 hr after transfection using a fluorescence microscope. (C) HTB-46 cells were cotransfected with RIα and GFP/RIAZ in the absence of cAMP. (D) RIAZ distribution after addition of cAMP for 8 hr.

Figure 11:
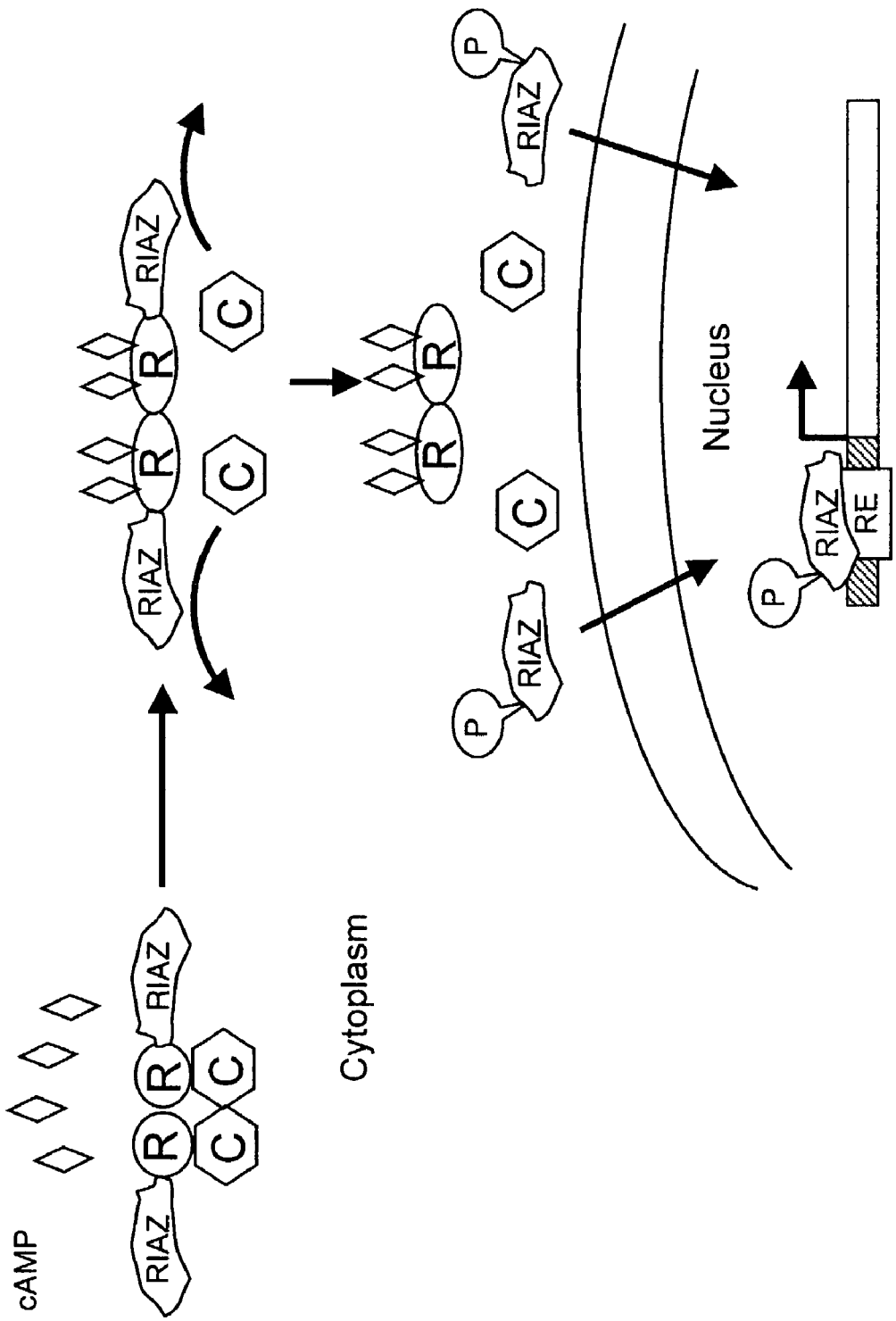

FIG. 11 depicts a model for the interaction of RIα with RIAZ in the holoenzyme complex of PKA. Binding of cAMP to the ternary complex of RIAZ/RI/C leads to the activation and phosphorylation of RIAZ by the C subunit. Phosphorylated RIAZ can translocate into the nucleus.

Figure 12:
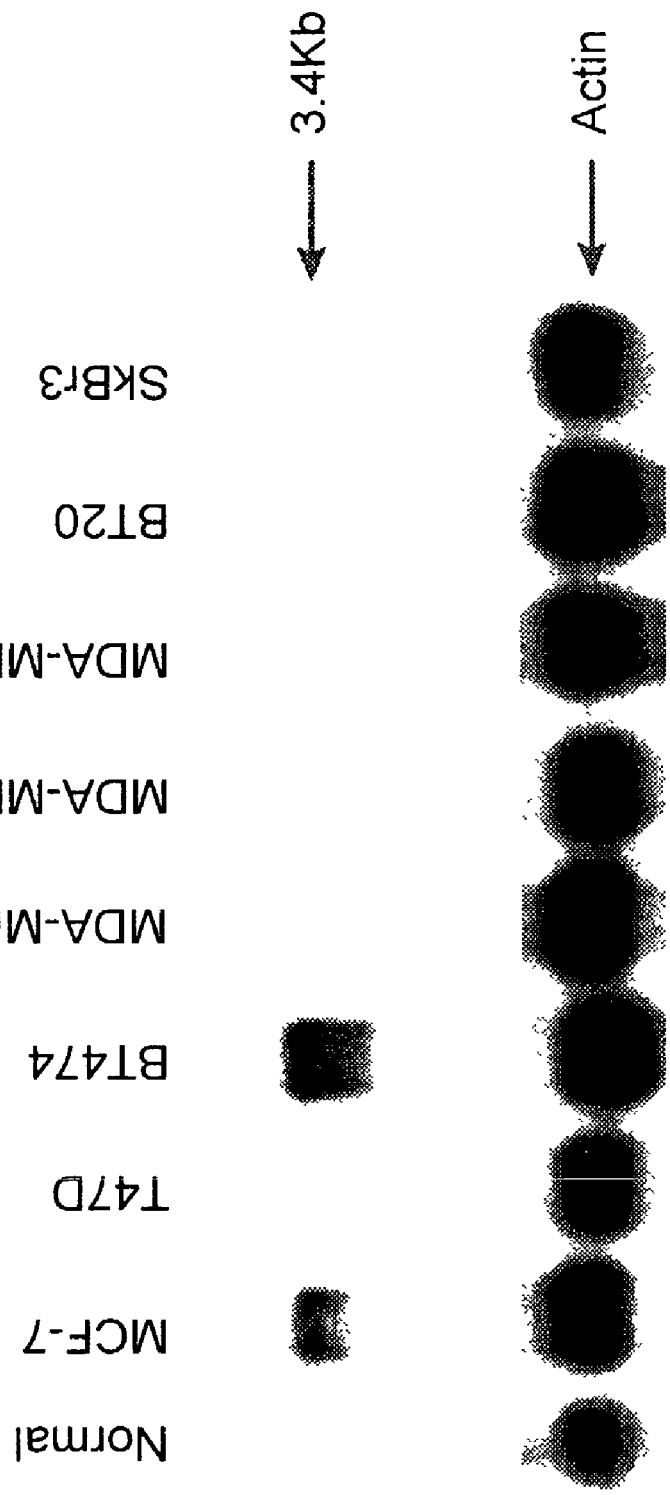

FIG. 12 shows Northern blot analysis of RIAZ expression in human breast cancer cell lines. Overexpression of RIAZ in human breast cancer cell lines is shown. RNAs were isolated from various human breast cancer cell lines and then analyzed by Northern blot. Compared to normal human breast tissue, RIAZ is overexpressed in MCF-7 and BT474 cells. Increased expression is also observed in SKBr3, BT20, MDA-MB-231, MDA-MB-435, MDA-MB-468, and T47D cells, suggesting a pathogenic role of RIAZ in breast carcinogenesis.

Figure 13:
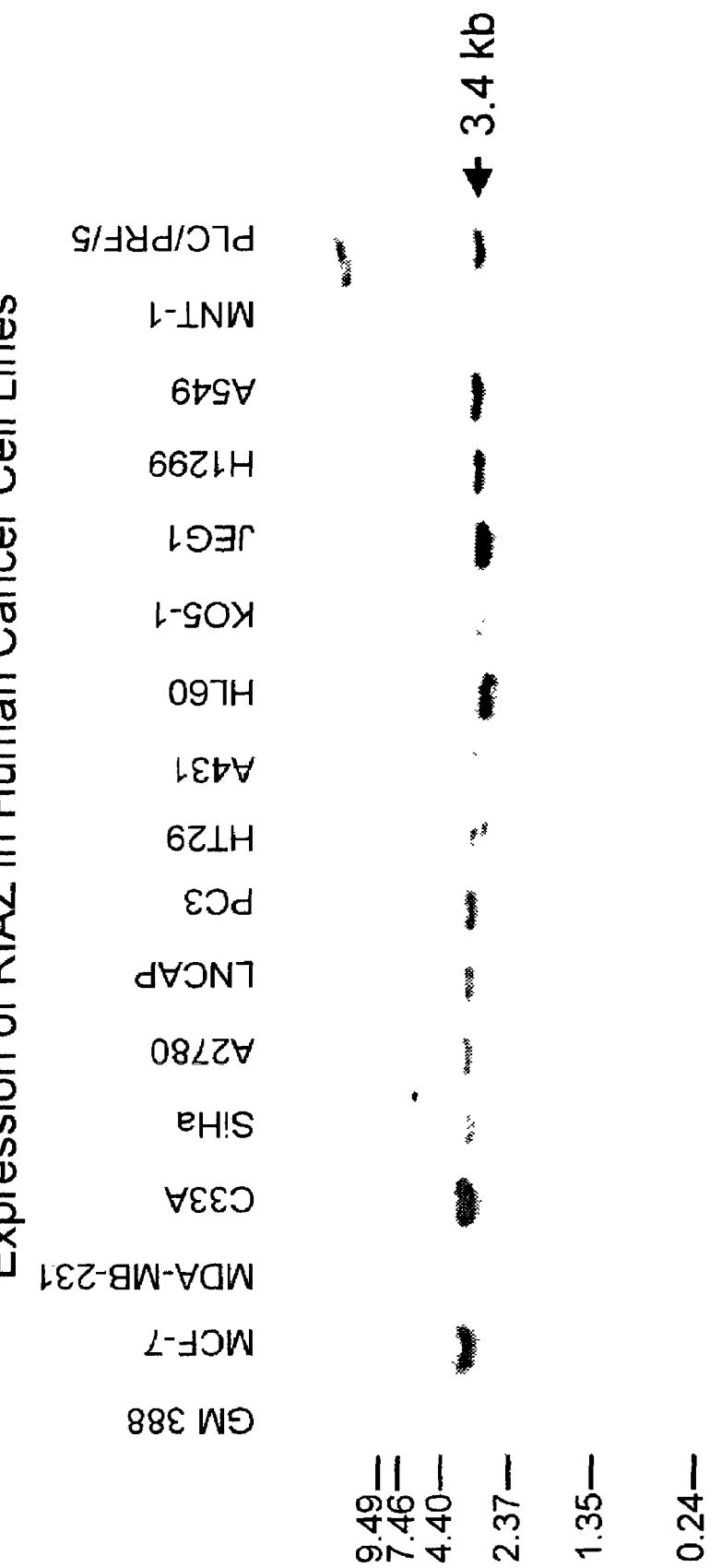

FIG. 13 shows Northern blot analysis of RIAZ expression in various human cancer cell lines. RNAs were isolated form various human cancer cell lines and than subjected to Northern blot analysis. Compared to normal fibroblast RIAZ is overexpressed in the breast carcinoma MCF-7, cervical carcinova C33A, choriocarcinoma JEG1, and myeloid leukemia HL60 cells. Increased expression was also observed in SiHa (cervical cancer), A2780 (ovarian cancer), LnCAP and PC3 (prostate cancer), H1299 and A549 (lung cancer), and PLC/PRF/5 (liver cancer).

Figure 14:
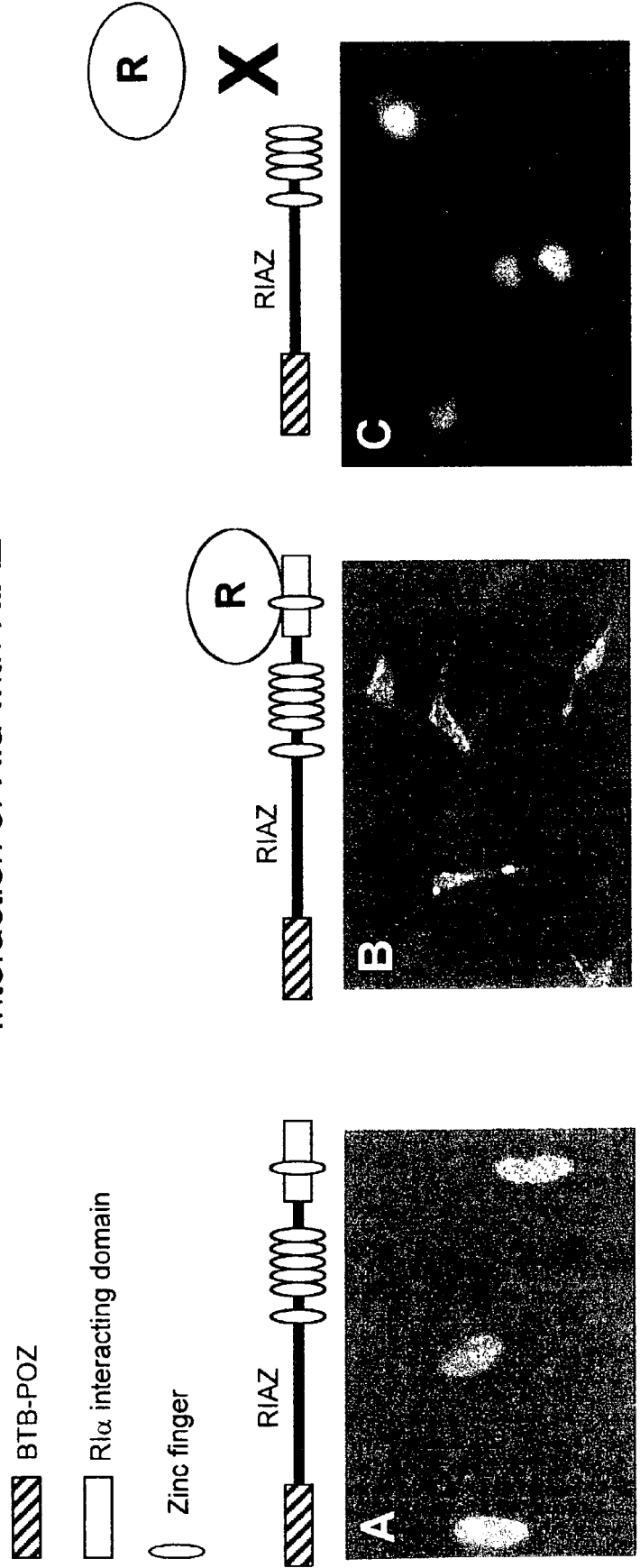

FIG. 14 depicts the interaction of RIhx as displayed graphically and the concomitant distribution of GFP/RIAZ on interaction with (i.e. in the presence of) RIα. A GFR/RIAZ construct lacking the C-terminal RIα-interacting region of RIAZ fails to redistribute to the cytoplasm on con-transfection with RIα. Panel (A) PC3M cells were transfected with GFP/RIAZ. Localization of RIAZ was visualized 24 hr. after transfection using a fluorescence microscope, and RIAZ was observed to be localized in the nucleus. Panel (B) PC3M cells were cotransfected with RIα and GFP/RIAZ and redistribution of RIAZ in the cytoplasm and nucleus was observed. Panel (C) Carboxy-terminus mutant or RIAZ was cotransfected with Rh. Inability to interact with RIα results in RIAZ localization confined in the nucleus.

Figure 15:
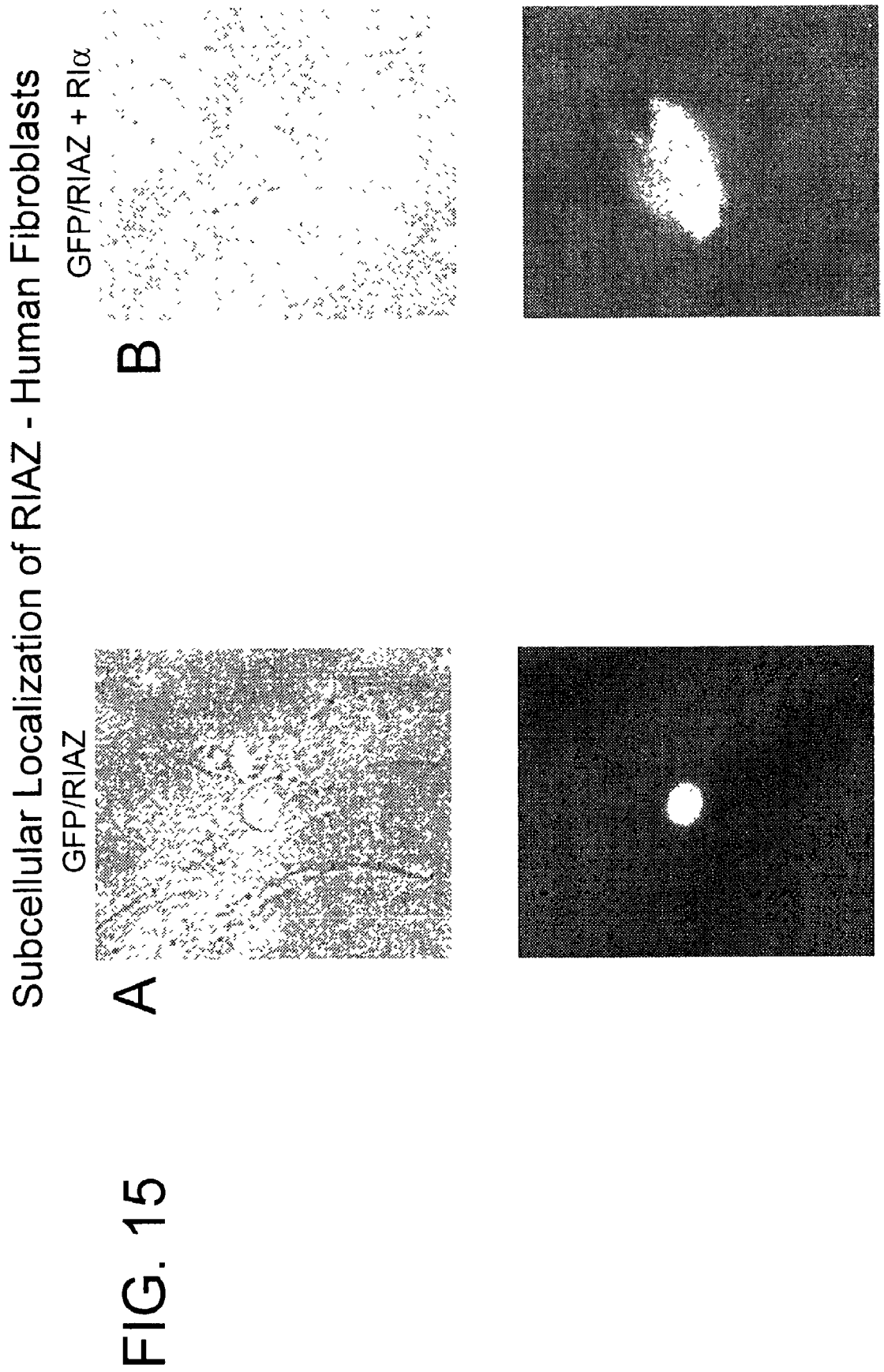
Figure 16:
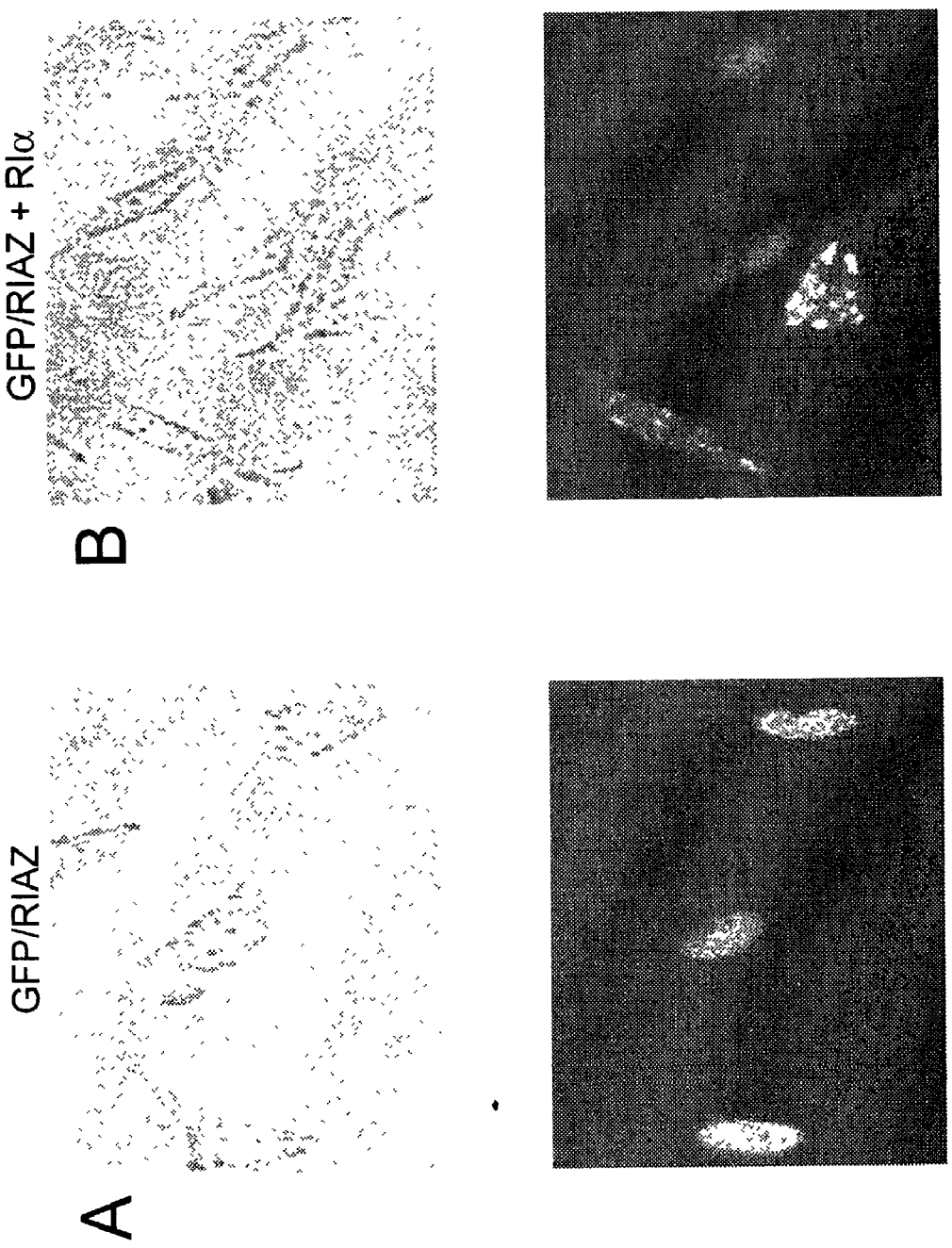

FIG. 15 depicts the subcellular localization in human fibroblasts of GFP/RIAZ in the absence and co-transfection of RIα. Nuclear localization of RIAZ and regulation of its localization by RIα in the human fibroblasts. Panel (A) Fibroblasts were plated the night before and then transfected with GFP/RIAZ the following day. Localization of RIAZ was visualized 24 hr after transfection using a fluorescence microscope. Panel (B) Fibroblast cells were cotransfected with RIa and GFP/RIAZ FIG. 16 depicts the subcellular localization in PCM3 prostate cancer cells of GFP/RIAZ in the absence and on co-transfection of RIα. Nuclear localization of RIAZ and regulation of its localization by RIα in the human prostate cancer PC3M cells. Panel (A) PC3M cells were plated the night before and then transfected with GFP/RIAZ the following day. Localization of RIAZ was visulaized 24 hr after transfection using a fluorescence microscope. Panel (B) PC3M cells were cotransfected with RIα and GFP/RIAZ.

DETAILED DESCRIPTION OF THE INVENTION

As stated above, the present invention relates the discovery of a factor associated with cAMP signalling that has been determined to play a role in transcription and concomitant activation of a plurality of stress responses, and that thereby may serve as a mediator of the transcriptional response to stress and thus, the multistress response in mammals, including humans.

As a first aspect of the invention, the stress response mediating factor identified and named herein RIα Interacting Zinc Finger Protein (RIAZ) is disclosed and has an sequence as set forth in FIG. 9 herein. The invention extends to RIAZ, antigenic fragments, analogs and mimics thereof, as well as the nucleic acids encoding RIAZ, and conserved variants thereof. Likewise, the invention extends to diagnostic methods, including drug discovery assays, that will in one embodiment, examine biological samples for the detection of the presence and amount of RIAZ, and that will thereby determine the susceptibility or onset of the patient or host to conditions such as cancer, with a variety of such cancers being contemplated and exemplified herein. As is presented hereinafter, RIAZ is present and is expressed in measurably significant excess in cancer cells such as breast cancer cells, prostate cells, and other tumor cells, so that the detection of RIAZ levels as part of a diagnostic test, can serve as a meaningful clinical indicator of patient condition and prognosis, as well as offering a succinct guide for therapy.

Likewise, as stated herein, RIAZ is believed to play a role in drug resistance in cancer, and therefore may be used in a variety of therapeutic protocols, including methods for modulating the expression of RIAZ, and in a particular embodiment, a method for inhibiting expression to thereby control the advance of a particular cancer. Such methods would include techniques including gene therapy, whereby an element known to suppress RIAZ expression could be introduced ex-vivo to a target colony of cells that could either be implanted in the host, or particular cells in the host could be modified in vivo, all in accordance with known techniques. Likewise, techniques including the use of antisense constructs, could be employed to control RIAZ expression.

As stated earlier, the nucleic acid encoding RIAZ is set forth in FIG. 9, and is known to be approximately 70 kDa in molecular weight. Active fragments and conserved variants thereof are contemplated for use in the gene therapy methods set forth above.

The following examples are presented below, which illustrate the characteristics and activities of the proteins and nucleic acids of the invention and are provided as being exemplary thereof. The examples are presented in order to more fully illustrate the preferred embodiments of the invention, and should in no way be construed, however, as limiting the broad scope of the invention.

EXAMPLE 1

Introduction

We have recently shown that genetic mutants derived from the CHO or the mouse adrenocortical carcinoma cells with defective RIα subunit exhibit resistance to the chemotherapeutic DNA damaging agent cisplatin (Liu, B. et al (1996) Cell Growth and Diff. 7:1105–1112). In contrast, C subunit mutants have comparable sensitivity to wild-type cells. These results suggest that, apart from inhibiting the C subunit, the RIα subunit may have novel physiological functions and may regulate drug resistance in cancer. Consequently, we propose that the RIα subunit may interact with other target proteins and regulate their functions in a cAMP-dependent fashion. To further understand the function of the R subunit, we examined by interaction cloning experiments using RIα subunit as bait and found it to interact with the cytochrome c oxidase subunit vb (CoxVb) (Yang, W. L. et al (1998) Biochemistry 37:14175–14180). Interaction was detected in vitro with a GST-RIα fusion protein as well as by coimmunoprecipitation with cell extracts. Deletion analysis showed that CoxVb binds to the amino terminus of RIα. Treatment with cAMP-elevating agents inhibited cytochrome c oxidase activity in CHO cells. These results support a novel mechanism of cAMP signaling through the interaction of RIα with CoxVb thereby regulating the activity of the cytochrome c oxidase complex and the release of cytochrome c from the mitochondria.

In these studies presented herein, we demonstrate that RIα also interacts with a novel zinc finger protein, which we term RIα-associated zinc finger (RIAZ). The protein is characterized by the presence of a BTB-POZ domain at its N-terminus and 7 zinc finger motifs of the $C_2H_2$-Kruppel type near its C-terminus. BTB (for Broad, tramtrack and bric a brac) or POZ (for poxviruses and zincfinger) domain is a newly characterized protein-protein interaction interface. We have cloned and sequenced the full length cDNA of the gene expressing this protein. We demonstrate that in vitro synthesized RIAZ protein interacts with RIα. Other members of this family of BTB/POZ domain zinc finger proteins have been shown to be involved in apoptosis, transcription repression and growth regulation. Furthermore, resistance to apoptosis may be a principal mechanism whereby tumors acquire resistance to anticancer drugs. Based on these observations, we hypothesize that the interaction of RIα with RIAZ may regulate apoptosis, cell growth and drug resistance, in particular cisplatin resistance.

R Subunit and Drug Resistance

It was shown previously that PKA mutants with decreased kinase activity exhibit increased sensitivity to various drugs that are substrates for P-glycoprotein including vinblastine and adriamycin. We demonstrated subsequently that the increased sensitivity to these drugs is due to a decreased expression of P-glycoprotein, thus explaining the elevated sensitivity to the MDR drugs (Cvijic, M. E. and Chin, K. V. (1997) Cell growth and Diff. 8:1243–1247. In the course of determining the mechanisms that regulate P-glycoprotein expression by PKA, we found the mouse Y1 adrenocortical carcinoma and the Chinese hamster ovary (CHO) cells harboring defective RIα subunit of PKA to exhibit increased resistance to cisplatin (Liu, B. et al (1996) Cell growth and Diff. 7:1105–1112). However unexpectedly, three independently derived C subunit mutants of CHO cells, which have decreased PKA activity, were equally sensitive to cisplatin as the wild-type cells. These results suggest that the RIα subunit of PKA, independent of the C subunit, may be involved in cellular sensitivity to cisplatin. To test this hypothesis, we further examined CHO cells transfected with a mouse dominant mutant RIα cDNA and found these cells to be more resistant to cisplatin than wild-type cells, thus further supporting our hypothesis that RIα may act independently of the kinase to modulate cellular sensitivity to chemotherapeutic agents.

Additional evidence that support R subunit's role in drug resistance is found in studies on multidrug resistance. The C subunit mutants of CHO cells have similar sensititvity as wild-type cells to P-glycoprotein substrates such as adriamycin, taxol and colchicine. No changes in P-glycoprotein expression was observed with these C subunit mutants compared to the wild-type cells. We speculate that the decreased mdr gene expression in the RIα subunit mutants may be due to the altered functions of the RIα mutant and not the altered kinase activity.

Figure 1:
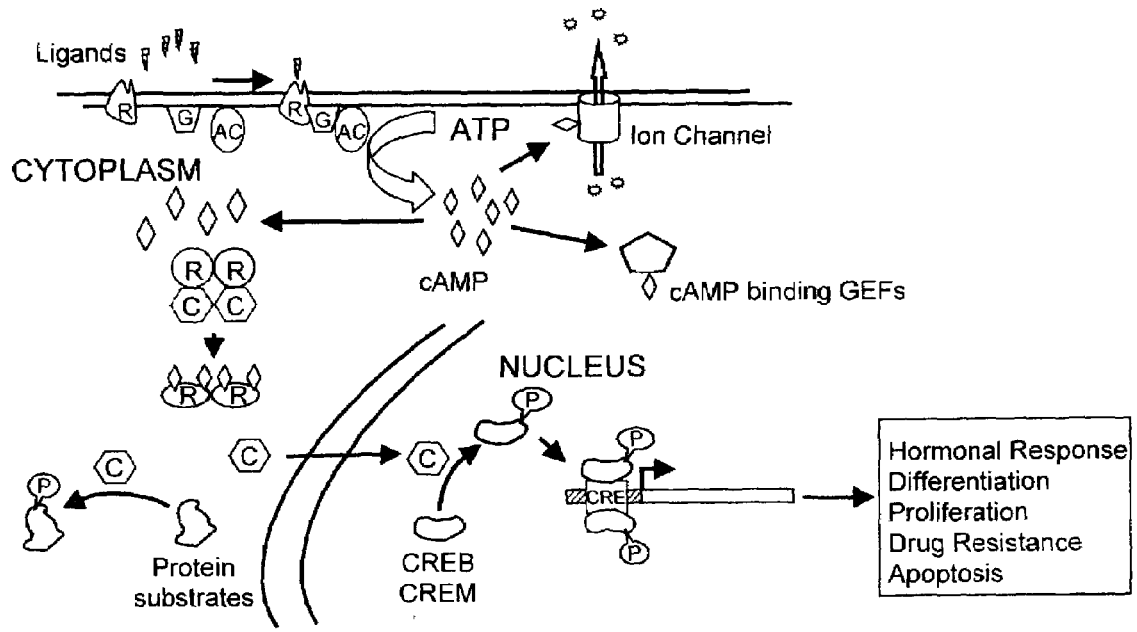
FIG. 1. The cAMP signal transduction pathway. Ligands at the cell surface interact with membrane receptors (R) and result in altered gene expression. Ligand binding activates coupled G-proteins (G) which in turn stimulates the activity of the membrane-associated adenylyl cyclase (AC). This converts ATP to cAMP which causes the dissociation of the inactive tetrameric holoenzyme PKA complex into the active catalytic subunits (C) and the dimeric cAMP-bound regulatory subunits (R). Catalytic subunits either phosphorylate substrate proteins in the cytoplasm or migrate into the nucleus where they phosphorylate and thereby activate transcriptional activators such as CREB (CRE-binding protein) and CREM (CRE-binding modulator). These factors bind as dimers to cAMP-response elements (CREs) found in promoters of cAMP-responsive genes to activated transcription. This event leads to the regulation of key physiological functions. Alternatively, cAMP may also bind directly to other receptor proteins such as ion channels and the cAMP-binding guanine nucleotide exchange factors (GEFs) and influence their functions.
Figure 2:
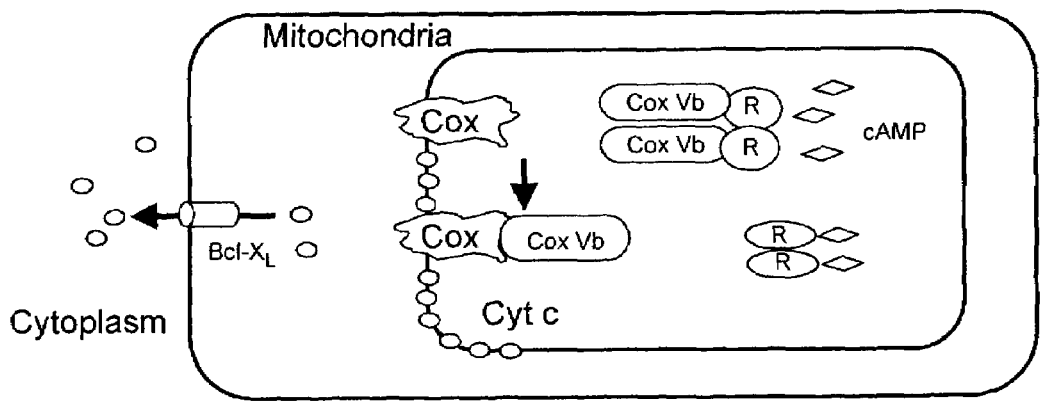
FIG. 2. A model for the interaction of RIα with CoxVb, the regulation of Cox activity and the release of cytochrome c from the mitochondria.

To assess the function of RIα subunit, we showed by interaction cloning experiments the association of cytochrome c oxidase subunit Vb (CoxVb) with RIα subunit (Yang, W. L. et al (1998) Biochemistry 37:14175–14180). The interaction is regulated by cAMP and the cytochrome c oxidase activity in CHO cells is inhibited by cAMP-elevating agents, with a concomitant decrease in cytochrome c levels in the mitochondria and an increase in its release into the cytosol. Furthermore, mutant cells harboring a defective RIα show increased cytochrome c oxidase activity and also constitutively lower levels of cytochrome c in comparison to either the wild-type cells or the C subunit mutant. These results suggest a novel mechanism of cAMP signaling through the interaction of RIα with CoxVb. We propose that growth inhibitory signals that elevate cAMP levels cause the dissocaition of CoxVb from RIα, thus enabling CoxVb to complex with cytochrome c oxidase, thereby inhibiting cytochrome c oxidase activity. Inhibition of the oxidase activity leads to an increase in cytochrome c release from the inner membrane of the mitochondria to the cytosol via pore channel formed by Bcl-XL (FIG. 2).

cAMP Signaling and R Subunit Mediated Drug Resistance

The potential role of PKA in modulating cellular responses to chemotherapeutic agents has been investigated. Recent studies have focused on the role of PKA in drug resistance and have attempted to exploit the cAMP signaling pathway to sensitize cancer to chemotherapy. It was shown that overexpression of the wild-type RIα subunit gene in CHO cells via retroviral-mediated gene transfer confers hypersensitivity to topoisomerase inhibitors. Additionally, the ADR-5 mutant derivative of CHO-K1 cells, which shows hypersensitivity to topoisomerase II poisons, is sensitive to 8-Cl-cAMP and overexpresses the endogenous RIα subunit. In another study that examined the effects of 8-Cl-cAMP on cisplatin-resistant PC-14 non-small cell lung carcinoma cells, it was shown that a low RI/RII ratio increases resistance to cisplatin; lending further support to the hypothesis that RIα deregulation or inactivation can alter cellular sensitivity to cisplatin.

To demonstrate unambiguously that the RIα subunit of PKA may modulate cellular sensitivity to anticancer agents, we overexpressed RIα in the human ovarian carcinoma A2780 cells and their cisplatin-resistant derivative CP70 using retrovirus carrying the human wild-type RIα cDNA (Cvijic, M. E. and Chin, K. V. (1998) BBRC 249:723–727). Our results showed that overexpression of RIα sensitizes the ovarian cancer cells to cisplatin. More importantly, high levels of RIα expression partially reverse cisplatin resistance in the drug resistant ovarian cancer cells. These and the above results taken together are consistent with our observations, and suggest that alterations of RIα subunit levels or activity may influence cellular sensitivity to chemotherapeutic agents.

In addition, studies using pharmacological agents that modulate cAMP levels showed that treatment of ovarian carcinoma cells with either forskolin or 3-isobutyl-1-methylxanthine causes an increase in cisplatin sensitivity compared to untreated cells. The putative phosphodiesterase inhibitor, dipyridamole, also acted synergistically with cisplatin to enhance cytotoxicity of both sensitive and resistant human ovarian cancer cells by 65%. Dipyridamole treatment did not affect the growth of cisplatin-resistant cells. The chemosensitizing effect of dipyridamole on cisplatin has also been demonstrated in vivo in animals bearing human bladder cancer and human testicular embryonal germ cell carcinoma that were treated simultaneously with both cisplatin and dipyridamole. Dipyridamole alone is not cytotoxic, however, its presence significantly enhanced the effects of cisplatin in a dose-dependent fashion, achieving complete tumor regression at high concentrations of dipyridamole.

It has also been reported in a number of studies that caffeine and other methylxanthines can potentiate the cytotoxicity of UV and ionizing radiation, as well as some cytotoxic agents including cisplatin. It is thought that part of the effects of the methylxanthines results from their inhibition of DNA repair. However, the mechanism by which this effect occurs is unclear and no direct evidence for the inhibition of repair enzymes by these agents has been demonstrated. Since dipyridamole and the methyixanthines including caffeine, pentoxifylline and isobutylmethylxanthine are all capable of raising the intracellular levels of cAMP by inhibiting cAMP phosphodiesterases, part of their mechanism of action in potentiating cisplatin-, UV and ionizing radiation-induced cytotoxicity may be attributable to the PKA signalling pathway mediated by cAMP. In light of our results with the PKA mutants and the phosphodiesterase and RIα transfectants, it is conceivable that the intended effects of these agents on DNA repair may be mediated by the R subunit.

The mechanism by which RIα regulates cellular sensitivity to anticancer agents is unclear and may not be related to its interaction with CoxVb and the release of cytochrome c from the mitochondria (FIG. 2), since the release of cytochrome c in CHO cells in response to cAMP does not lead to cell death, but growth arrest. We now have further evidence that RIα interacts with a novel BTB-POZ domain zinc finger protein which we termed RIα-associated zinc finger (RIAZ). In vitro synthesized RIAZ protein also interacts with RIα. Recent studies with other highly conserved members of the BTB-POZ domain zinc finger transcription factor suggest that they may be involved in cell growth regulation, transcription repression, and apoptosis. Furthermore, resistance to apoptosis may be a principal mechanism whereby tumors acquire resistance to anticancer drugs. These properties of the BTB-POZ proteins seem to be consistent with the effects of cAMP or RIα in drug resistance and cell growth observed in our studies. Based on these observations, we hypothesize that the interaction of RIα with RIAZ and its regulation by cAMP is a novel signaling mechanism of the cAMP messenger system, and may regulate apoptosis, cell growth and drug resistance.

Anticancer drug resistance mediated by the cAMP signaling pathway or the R subunit of PKA may be important mechanisms whereby tumors can acquire resistance. We speculate further that the therapeutic efficacy of using cAMP-modulating agents in combination with cisplatin and other chemotherapeutic agents may have significant impact for the treatment of human cancers. Hopefully through our studies of the interaction of RIα with RIAZ, the molecular mechanisms of resistance due to the cAMP signaling pathway through RIα interaction can be better defined.

Programmed cell death or apoptosis may be the primary mechanism by which anticancer drugs effect their responses. Resistance to apoptosis, therefore, may be a principal mechanism that tumors may acquire to become resistant to chemotherapeutic drugs. The transcription factor $NF_\kappa B$ is activated by chemotherapy and by irradiation in some cancer cell lines. Furthermore, inhibition of $NF_\kappa B$ in vitro leads to enhanced apoptosis in response to a variety of different stimuli. It was shown recently that inihibition of $NF_\kappa B$ with a modified form of $I_\kappa B\alpha$ sensitizes drug resistant tumors to the effects of CPT-11, a camptothecin analog, and TNFα. These results demonstrate that the activation of $NF_\kappa B$ in response to chemotherapy is a principal mechanism of inducible tumor chemoresistance, and establish the inhibition of $NF_\kappa B$ as a new approach to adjuvant therapy in cancer treatment.

Results

Interaction of RIα with a Novel BTB-POZ Domain Zinc Finger Protein

Figure 3:
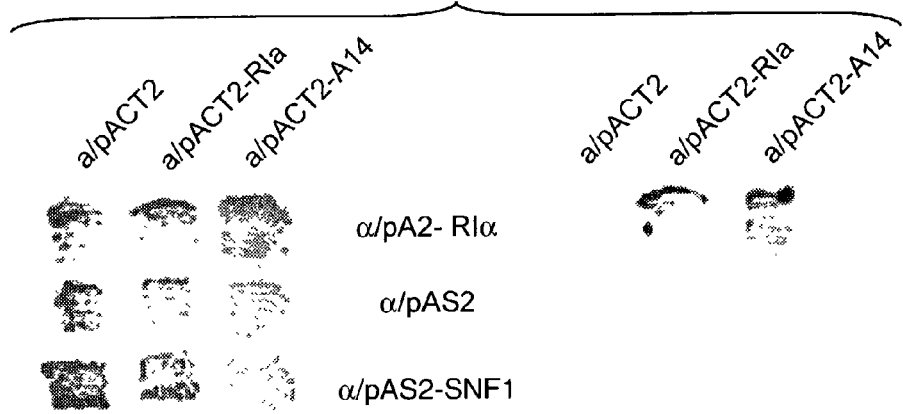

Our results thus far implicate that RIα may play a role in regulating drug resistance. However, the molecular mechanisms of resistance mediated by RIα via the cAMP pathway is unclear and cannot be explained by its interaction with CoxVb and the release of cytochrome c from the mitochondria (FIG. 2); since the release of cytochrome c in CHO cells in response to cAMP results in growth arrest but not cell death. To further determine the mechanism of RIα in drug resistance, we examined the interaction of RIα subunit with a novel BTB-POZ domain zinc finger protein identified from a yeast two-hybrid interaction screen (Fields, S. (1993) Meth. Enzymol. 5:116–124) in a human liver cDNA library, constructed in the GAL4 activation domain vector pGAD10. After screening the library, a positive RI a-interacting clone pACT2-A14 was isolated. The interaction between RIα and pACT2-A14 was verified by yeast mating assay. Results in FIG. 3 showed positive interaction between RIα and pACT2-A14. No interaction was observed with the negative control snfl protein kinase. Since RIα forms a dimer in the holoenzyme, thus interaction of RIα with itself was used as a positive control.

Pull down assay using the GST-RIα fusion protein and its deletion mutants expressed in *E. Coli* was then used to examine their interactions with pACT2-A14 from yeast lysates and to determine the domain that is required for the interaction. There are two domains on RIα that may be important for its interaction, the amino terminal dimerization region and the carboxyl terminus that includes the autoinhibitory region, and the two tandem cAMP binding sites (FIG. 4A). Two RIα deletion mutants were made, the amino terminal deletion mutant GST-RIα(Δ1–76) and the carboxyl terminal deletion mutant GST-RIα(Δ77–380). As shown in FIG. 4B, deletion of the C-terminus of RIα, GST-RIα(Δ77–380), that includes the autoinhibitory region and the two cAMP binding sites, did not significantly affect its association with pACT2-A14, while deletion of the amino terminal end, GST-RIα(Δ1–76), containing the dimerization as well as the A-kinase anchoring protein (AKAP) binding domains virtually abolished its interaction with pACT2-A14. These results suggest that association of RIα with pACT2-A14 occurs either at the dimerization domain or at the site required for AKAP binding.

Sequence analysis of clone pACT2-A14 shows that it is an anonymous expressed sequence tag (EST) with significant homology to a large number of zinc finger proteins. Northern blot analysis showed that the putative gene is expressed at significant levels in many normal human tissues (FIG. 5). The gene is expressed at significantly high level in the spleen, ovary, and heart. Moderate levels are detected in testis, leukocytes and brain. The apparent molecular size of the mRNA that pACT2-A14 hybridized to is approximately 3.4 kb. We cloned and sequence the gene from a human fetal brain cDNA library (FIG. 9). Further analysis of the full length sequence identified an open reading frame that encodes a novel putative BTB-POZ domain zinc finger protein of 641 amino acids (starting from nucleotide position 467–2390) with a calculated molecular mass of 69 kDa, which we termed RIα-associated zinc finger (RIAZ). A schematic structure of RIAZ is shown in FIG. 6. The protein is characterized by the presence of a BTB-POZ domain at its N-terminus and 7 zinc finger motifs of the $C_2H_2$-Kruppel type near its C-terminus. BTB (for Broad, tramtrack and bric a brac) or POZ (for poxviruses and zincfinger) domain is a newly characterized protein-protein interaction interface (Albagli, O. et al (1995) Cell growth Differ. 6:1193–1198). Studies on BTB-POZ domain, an approximately 120-amino acid region, have revealed that it is evolutionarily highly conserved and found generally at the N-terminus of actin-binding as well as nuclear DNA-binding proteins. Recent studies with other highly conserved members of the BTB-POZ domain zinc finger transcription factor suggest that they may be involved in cell growth regulation (Reuter, S. et al (1998) EMBO J. 17:215–222; dela Luna, S. et al (1999) EMBO J. 18:212–228), transcription repression (Okabe, S. et al (1998) Mol. Cell. Biol. 18:4235–4244; Deweindt, C. et al (1995) Cell growth Differ. 6:1495–1503), and apoptosis (Yamochi, T. et al (1999) Oncogene 18:487–494). In *Drosophila melanogaster*, the BTB-POZ domain protein group is made up of transcription factors which play key roles in a variety of developmental programmes (Albagli, O. et al (1995) Cell growth Differ. 6:1193–1198). The mammalian group includes BTB-POZ domain proteins involve in transcription repression. They can also be important in influencing tumorigenesis as, for e.g., the gene encoding LAZ3/BCL6 (lymphoma-associated zinc finger 3/B cell lymphomas 6) frequently is altered by chromosomal translocation, small deletions and point mutations in non-Hodgkin lymphomas (Kerckaert, J. P. et al (1993) Nat. Genet. 5:66–70; Ye, B. H. et al (1993) Science 262:747–750). Similarly, in a subset of acute promyelocytic leukemia, PLZF (promyelocytic leukemia zinc finger) is fused to the RARα (retinoic acid receptor α) gene (Chem, Z. et al (1993) EMBOJ. 12:1161–1167). These studies imply that some BTB-POZ domain proteins have an important role in regulating cell proliferation.

In vitro-translated isotope-labeled RIAZ showed a molecular size of approximately 67–70 kDa, which is close to its calculated molecular weight based on the putative open reading frame of the cloned cDNA (FIG. 7). Deletion of a cluster of ATG in the 5' end of the RIAZ cDNA seemed to enhance translation from the putative ATG start codon of the open reading frame that encode the BTB-POZ domain zinc finger. In addition, the in-vitro translated RIAZ protein showed binding to GST-RIα but not to GST control (FIG. 8). These results demonstrate that RIAZ, a novel putative BTB-POZ domain zinc finger transcription factor, interacts with the RIα subunit of PKA. In addition, based on the functions of other BTB-POZ zinc finger proteins in this family, which play various roles in apoptosis, transcription repression, and regulation of cell proliferation, we speculate that RIAZ may have a role in these important cellular functions. Since the emergence of drug resistance in cancer is also intimately influenced by apoptosis, alterations in cellular transcription programs and tumorigenesis, therefore, it is conceivable that RIα mediated drug resistance may be executed through the actions of RIAZ. Biochemical and molecular characterizations of the interaction of RIAZ with RI and its function and significance in drug resistance may yield insights into the mechanisms of this novel cAMP signaling pathway.

EXAMPLE 2

Abstract

In the course of our investigation for proteins that interacts with the RIα subunit of PKA that may play a role in cisplatin resistance (Yang, W.-L. et al (1998) Biochemistry 37:14175–14180), we have identified a novel BTB-POZ domain zinc finger transcription factor that interacts with RIα. Sequence analysis of this novel factor, which we termed RIAZ, reveals that it is an ortholog of the yeast S. cerevisiae Msn2p/Msn4p multistress response transcription factors, sharing approximately 25% identity in the amino acid sequence and about 48% sequence similarity. Furthermore, in co-transfection studies RIα sequesters RIAZ in the cytoplasm and elevation in cAMP levels causes a redistribution of RIAZ into the nucleus. Based on these results, we hypothesize that RIAZ may be a multistress response transcription factor in higher eukaryotes regulated by cAMP. These findings present a novel mechanism of cAMP signaling and a potentially hitherto unidentified multistress response pathway in higher eukaryotes. Therefore, the foregoing supports the observation herein that RIAZ acts as a multistress response protein that coordinates and reprograms the transcription profiles of higher eukaryotes to adapt to various environmental stresses.

Introduction

We have identified a novel BTB-POZ domain zinc finger transcription factor, denoted RIAZ, which may be functionally related to the Saccharomyces cerevisiae Msn2p and Msn4p zinc finger proteins. Msn2p/Msn4p are DNA binding proteins and are the transcriptional activators of the multistress response in S. Cerevisiae stimulated by a remarkable variety of stresses that includes in addition to heat shock, DNA alkylation, osmotic shock, oxidative damage, heavy metal exposure, and certain types of nutrient deprivations. Transcriptional control by multiple stress is mediated by the stress response element (STRE). Msn2p/Msn4p recognize and bind STREs. The yeast cAMP-dependent protein kinase activity (PKA) is a powerful repressor of STRE-mediated transcription. In addition, it has also been shown that the BTB-POZ domain zinc finger family of proteins are involved in development, transcription repression, cell proliferation and apoptosis. We have shown in our preliminary data that this novel BTB-POZ domain zinc finger protein, which we termed RIAZ (RIα associated zinc finger), interacts with RIα and is sequestered in the cytoplasm. Exposure to cAMP causes translocation of RIAZ into the nucleus. Sequence analysis revealed that RIAZ exhibits approximately 25% identity to MSN2 and MSN4 in the amino acid sequence and approximately 48% similarity. We hypothesize that RIAZ may be a functional homolog of Msn2p/Msn4p, mediating the transcriptional response to various stress in mammalian cells. Further studies will focus on examining the mechanism of regulation of RIAZ by cAMP and multistress, and to elucidate the functions of RIAZ as a transcriptional activator of multistress response.

The ubiquitous signal transduction pathway of cAMP mediated by the cAMP-dependent protein kinase (PKA) is critically involved in the regulation of metabolisms, cell growth and differentiation, apoptosis and gene expression. The mechanism of cAMP-dependent signaling involves binding to the regulatory (R) subunit of PKA that leads to the dissociation of the holoenzyme and activation of the catalytic (C) subunit kinase. Transcriptional regulation by cAMP is mediated by a family of cAMP-responsive nuclear factors which contain the basic domain/leucine zipper motifs and bind to cAMP-responsive elements (CRE). The function of CRE-binding proteins (CREBs) is modulated by phosphorylation by PKA. In the yeast Saccharomyces cerevisiae, PKA is implicated in the coordination of several essential cellular events like cell growth, entry into cell division, reprogramming of transcription during the switch of nutrient sources, and PKA also acts as a key repressor of stress response element (STRE)-mediated transcription. The yeast proteins Msn2p and Msn4p are multistress response transcription factors that activates STRE-regulated genes in response to heat shock, DNA damage, oxidative damage, heavy metal exposure and certain types of nutrient deprivation. Msn2p and Msn4p translocate from the cytoplasm to the nucleus in a stress-dependent manner and high PKA activity reverses the nuclear localization under stress conditions. Msn2p and Msn4p recognize and bind STREs. Sequence analysis now reveals that RIAZ may be a mammalian functional homolog of Msn2p and Msn4p. RIAZ exhibits approximately 25% identity to MSN2 and MSN4 in the amino acid sequence and approximately 48% similarity.

We previously showed that in vitro synthesized RIAZ protein interacts with RIα (see Example 1 above). We demonstrate in this Example that cotransfection of RIAZ with RIα resulted in the sequestration of RIAZ in the cytoplasm and upon exposure to cAMP, RIAZ translocates into the nucleus. These characteristics of RIAZ are similar to Msn2p/Msn4p. Furthermore, members of the emerging family of BTB/POZ domain zinc finger transcription factors have been shown to be involved in apoptosis, transcription repression, and growth regulation. Based on these observations, we hypothesize that RIAZ may have similar functions in mammalian cells as those of Msn2p/Msn4p and BTB-POZ zinc finger protein, in regulating apoptosis, cell growth and multistress response.

Results

RIAZ is an Ortholog of Yeast Multistress Response Factors Msn2p and Msn4p

Further analysis of the putative amino acid sequence of RIAZ reveals that it is an ortholog of the yeast multistress response zinc finger transcription factors Msn2p and Msn4p (Martinez-Pastor, M. T. et al (1996) EMBO J. 15:2227–2235; Schmitt, A. P. and McEntee, K. (1996) Proc. Natl. Acad. Sci. USA 93:5777–5782; Estruch, F., and Carlson, M. (1993) Mol. Cell. Biol. 13:3872–3881). In addition, since type I PKA is predominantly localized in the cytoplasm (Deviller, P. et al (1984) Mol. Cell. Endocrinol. 38:21–30) and that RIα subunit has been shown to bind tightly to the plasma membrane (Rubin, C. S. et al (1972) J. Biol. Chem. 247:6135–6139), therefore, RIAZ should colocalize with RIα in the cytoplasm. Therefore, like Msn2p/Msn4p, RIAZ may be a novel RIα subunit and cAMP-regulated cytoplasmically localized transcription factor. These results suggest the exciting possibility that RIAZ is a highly evolved multistress response transcription factor in mammalian cells, that possesses two signature structural features, the BTB-POZ domain and the DNA binding zinc finger moiety.

In our preliminary studies, we have demonstrated the interaction of RIα with a novel BTB-POZ domain zinc finger protein, RIAZ. Sequence analysis revealed that RIAZ may be an ortholog of the yeast Msn2p/Msn4p multistress response transcription factors. Furthermore, studies with BTB-POZ domain zinc finger transcription factors and Msn2p/Msn4p have already shown that these proteins play important roles in apoptosis, cell proliferation, transcription repression and multistress response (Moskvina, E. et al (1999) Mol. Microbiol. 32:1263–1272; Albagli, O. et al (1995) Cell Growth Differ. 6:1193–1198; Reuter, S. et al (1998) EMBO J. 17:215–222; de la Luna, S. et al (1999) EMBO J. 18:212–228; Okabe, S. et al (1998)Mol. Cell. Biol. 18:4235–4244; Deweindt, C. et al (1995) Cell Growth Differ. 6:1495–1503; Yamochi, T. et al (1999) Oncogene 18:487–494.). We thus hypothesized that like Msn2p/Msn4p, RIAZ may function as a cAMP-mediated multistress response transcription factor in mammalian cells. The following studies are designed to gain further understanding of the interaction of RIα with RIAZ and to elucidate the functions of RIAZ as a multistress response protein.

Nuclear Localization of RIAZ and Cytoplasmic Translocation on Interaction with RIα

Using RIα as bait, we had conducted a yeast two-hybrid screen and identified a novel transcription factor, which we have termed RIAZ, that interacts with RIα. RIAZ's deduced amino acid sequence revealed an amino-terminal BTB/POZ protein-protein interaction domain and seven carboxy-terminal zinc fingers of the $C_2H_2$ DNA-binding type. RIAZ thus belongs to a rapidly growing family of BTB-POZ zinc finger transcription factors that include the *Drosophila* developmental regulators Tramtrak and Bric a brac, and the human oncoproteins BCL-6 and PLZF, which are causally linked to non-Hodgkins' lymphoma and acute promyelocytic leukemia, respectively. Since BTB-POZ domain zinc finger proteins are transcription factors, presumably, they may be localized to the nucleus. However, type I PKA is predominantly localized to the cytoplasm (Deviller, P. et al (1984) Mol. Cell. Endocrinol. 38:21–30) and that RIα subunits have been shown to bind tightly to the plasma membrane (Rubin, C. S. et al (1972) J. Biol. Chem. 247: 6135–6139). Therefore, the interaction of RIα with RIAZ may sequester RIAZ in the cytoplasm. This differential localization raised the possibility that the interaction of RIα with RIAZ may be a novel mechanism of regulation of transcription factor in response to stress via the cAMP pathway.

To further understand the mechanisms of interaction of RIα with RIAZ, we constructed a hybrid protein between RIAZ and the green fluorescence protein (GFP), with GFP fused to either the N-terminal (GFP/RIAZ) or the C-terminal (RIAZ/GFP) end of RIAZ. Distribution of RIAZ was visualized using a Zeiss Axioskop fluorescence microscope. Images was scanned with a Quantix CCD camera using IP LAB software under Window 98, processed in Adobe Photoshop 5.0, and printed on a Kodak videoprinter. Localization patterns of either constructs were similar after transfection into the human renal carcinoma cells, HTB-46 (FIGS. 10A and 10B). Even though the nuclear localization of RIAZ was not affected by the position of GFP either at the amino or the carboxy terminal end of RIAZ, however, whether the transcriptional activity of RIAZ may be affected remains to be determined. Overexpression of RIAZ, like other BTB-POZ zinc finger proteins, resulted in its localization in the nucleus and was associated with specific nuclear dots (FIG. 10A). Interestingly, when GFP/RIAZ was cotransfected with RIα into the HTB-46 cells, RIAZ was redistributed predominantly in the cytoplasm (FIG. 10C), suggesting that RIAZ was sequestered by RIα in the cytoplasm as a result of the interaction. We then treated these cells with 8-Br-cAMP and found RIAZ to translocate to the nucleus subsequently upon activation (FIG. 10D). Interestingly, the distribution pattern of RIAZ in the nucleus after activation by cAMP is different from the uninduced punctate pattern. These results confirmed the interaction of RIAZ with RIα and suggest that RIAZ was sequestered by RIα in the cytoplasm. Upon treatment with cAMP, RIAZ dissociates from RIα and translocate into the nucleus. We propose that RIAZ may associate with RIα via the PKA holoenzyme complex (see FIG. 11). Upon cAMP binding to the R subunit, dissociation and activation of the C subunit enable it to phosphorylate RIAZ which leads to the dissociation of RIAZ from RIα and its translocation into the nucleus (FIG. 11). Sequence analysis revealed the presence of potential PKA phosphorylation consensus sites in RIAZ at serine residues 349 and 490. Further studies will be conducted to verify whether the phosphorylation of these serine residues are required for nuclear translocation or transcriptional activation by site-directed mutagenesis.

The carboxy-terminus of RIAZ is essential for interaction with RIα because deletion of the C-terminus abolishes the interaction with RIα. This is demonstrated in FIG. 14 where C-terminal deletion GFP-RIAZ constructs fail to interact with RIα subunit and were not redistributed to the cytoplasm in the presence of transfected RIα (FIG. 14, last panel).

RIAZ Expression is Increased in Cancer Cell Lines

To assess the expression of RIAZ in transformed and cancerous cells we have conducted Northern blot analysis with a panel of human breast cancer cell lines to determine the expression of RIAZ (FIGS. 12 and 13). Our results showed that RIAZ is expressed in high levels in MCF-7 and BT474 cells compared to the normal breast tissue. Low levels of RIAZ exSKBr3, BT-20, T47D, MDA-MB-231, MDA-MB-435, and MDA-MB-468), suggesting its role in growth control and tumorigenesis. In comparison to normal fibroblast cell line, RIAZ is also found to be overexpressed in a variety of other cancer cell lines including C33A (cervical cancer), HL60 (leukemia), JEG1 (choriocarcinoma), LnCAP and PC3 (prostate cancer) and others (FIGS. 12 and 13).

Interaction of RIAZ with RIα is further demonstrated in intact cells by transfection of the fusion construct of RIAZ with the green fluorescence protein (GFP), RIAZ/GFP. Upon transfection, the RIAZ/GFP fusion protein is localized in the nucleus of normal human fibroblasts, prostate and kidney carcinoma cells (FIGS. 15 and 16). Co-transfection with RIα resulted in a redistribution of RIAZ/GFP into both the cytoplasm and nucleus and that in the presence of cAMP, RIAZ translocated from the cytoplasm into the nucleus, thus authenticating the interaction of RIAZ with RIα and the regulation of RIAZ transcription by cAMP (FIGS. 15 and 16).

In view of its elevated expression in breast cancer cell lines and some other human tumor cell lines, our results suggest that RIAZ may play a role in cell growth regulation. Deregulated expression of RIAZ such as those in the breast cancer cell lines and other human tumor cell lines support its role in tumorigenesis. This pattern of RIAZ overexpression in breast cancer is reminiscent of those of the epidermal growth factor receptor and HER2/NEU oncogene overexpression in breast cancer. Therefore, RIAZ overexpression may serve as a marker for the detection of human cancer.

It has also been shown recently that RIα mutation may occur in some benign tumors. Such mutations suggest that RIα may play a role in tumorigenesis, perhaps in some early steps during tumor progression. More importantly, it was also demonstrated recently that RIAZ is targeted for translocation in Ewing sarcoma. Therefore, it is conceivable that the molecular interaction between RIAZ and RIα and its regulation by cAMP may be critical for cell growth control and that genetic alterations of RIAZ and RIα by either deregulation of expression, mutation and chromosomal translocation, contribute critically to tumorigenesis. Therefore, both RIAZ and RIα will be important markers as diagnostic and prognostic tools in cancer detection.

We have found previously that mutation in RIα increases cellular resistance to cisplatin, suggesting RI may have functions independent of the kinase activity. These findings were the foundation of the yeast two-hybrid screen to search for proteins that may interact with RIα, thus leading to the identification of RIAZ. Our results here also suggest that RIAZ may play a role in drug resistance in cancer in view of its interaction with RIα, and that mutation of RIα disrupt the functional interaction with RIAZ and subsequently deregulates growth control and alters tumors sensitivity to chemotherapeutic agents. Therefore, genetic changes in RIAZ may also serve as a marker for chemosensitivity in cancers.

Although the current invention has been described in connection with a specific form thereof, it is to be understood and appreciated that a wide array of equivalents may be substituted for the specific elements described and shown herein without departing from the spirit and scope of the invention.

RERERENCES

The text of the following references is incorporated herein by reference. The fact that these references are cited herein is not intended to indicate that the references provide prior art teachings of the invention.
1. Cisplatin resistance and regulation of DNA repair in cAMP-dependent protein kinase mutants (Liu, B., Cvijic, M. E., Jetzt, A. and Chin, K.-V., Cell Growth and Differ. 7:1105–1112, 1996).
2. Regulation of P-glycoprotein expression in cAMP-dependent protein kinase mutants (Cvijic, M. E., and Chin, K. V., Cell Growth and Differ. 8:1243–1247, 1997).
3. Overexpression of RIα on the Cisplatin Sensitivity of Human Ovarian Carcinoma Cells (Cvijic, M. E. and Chin, K.-V., Biocehm. Biophys. Res. Comm., 249:723–727, 1998).
4. Cisplatin sensitivity in cAMP-dependent protein kinase mutants of *Saccharomyces cerevisiae* (Cvijic, M. E., Yang, W.-L., and Chin, K.-V., Anticancer Res., 18:3187–3192, 1998).
5. A novel mechanism of cAMP signaling through the interaction of the regulatory subunit of protein kinase A with cytochrome c oxidase subunit Vb (Yang, W.-L., Iacono, L., Tang, W.-M., and Chin, K.-V., Biochemistry, 37:14175–14180, 1998).
6. Francis, S. H., and Corbin, J. D. (1994) Structure and function of cyclic nucleotide-dependent protein kinases. Annu. Rev. Physiol., 56:237–272.
7. Edelman, A. M., Blumenthal, D. K., Krebs, E. G. (1987) Protein serine/threonine kinases. Annu. Rev. Biochem., 56:567–613.
8. Taylor, S. S., Buechler, J. A., Yonemoto, Y. (1990) cAMP-dependent protein kinase: framework for diverse family of regulatory enzymes. Annu. Rev. Biochem., 59:971–1005.
9. Lalli, E., and Sassone-Corsi, P. (1994) Signal transduction and gene regulation: The nuclear response to cAMP. J. Biol. Chem., 269:17359–17362.
10. Cho-Chung, Y. S. (1990) Role of cyclic AMP receptor proteins in growth, differentiation, and suppression of malignancy: New approaches to therapy. Cancer Res., 50:7093–7100.
11. Gottesman, M. M., and Fleischmann, R. D. (1986) The role of cAMP in regulating tumor cell growth. Cancer Surveys, 5:291–308.
12. Gottesman, M. M. (1980) Genetic approaches to cyclic AMP effects in cultured mammalian cells. Cell, 22:329–330.
13. Liu, F. C., Takahashi, H., McKay, R. D., and Graybiel, A. M. (1995) Dopaminergic regulation of transcription factor expression in organotypic cultures of developing striatum. J. Neurosci., 15:2367–2384.
14. Zufall, F., Shepherd, G. M., and Barnstable, C. J. (1997) Cyclic nucleotide gated channels as regulators of CNS development and plasticity. Curr. Opin. Neurobiol., 7:404–412.
15. Santoro, B., Liu, D. T., Yao, H., Bartsch, D., Kandel, E. R., Siegelbaum, S. A., and Tibbs, G. R. (1998) Identification of a gene encoding a hyperpolarization-activated pacemaker channel of brain. Cell, 93:717–729.
16. Zhong, H., Yang, H. S., Erdjument-Bromage, H., Tempst, P., and Ghosh, S. (1997) The transcriptional activity of NF-kB is regulated by the IkB-associated PKAC subunit through a cyclic AMP-independent mechanism. Cell, 89:413–424.
17. De Rooij, J., Zwartkruis, F. J. T., Verheijen, M. H. G., Cool, R. H., Nijman, S. M. B., Wittinghofer, A., and Bos, J. L. (1998) Epac is a Rap1 guanine nucleotide-exchange factor directly activated by cyclic AMP. Nature, 396: 474–477.
18. Kawasaki, H., Springett, G. M., Mochizuki, N., Toki, S., Nakaya, M., Matsuda, M., Housman, D. E., and Graybiel, A. M. (1998) A family of cAMP-binding proteins that directly activates Rap1. Science, 282:2275–2279.
19. Gergley, P. and Bot, G. (1977) The control of phosphorylase phosphatase by cAMP-dependent protein kinase. FEBS Letters, 82:269–272.
20. Khatra, B. S., Printz, R., Cobb, C. E., and Corbin, J. D. (1985) Regulatory subunit of cAMP dependent protein kinase inhibits phosphoprotein phosphatase. Biochem. and Biophy. Res. Comm., 130:567–572.
21. Srivastava, R. K., Lee, Y. N., Noguchi, K., Park, Y. G., Ellis, M. J., Jeong, J. S., Kim, S. N., Cho-Chung, Y. S. (1998) The RIIbeta regulatory subunit of protein kinase A binds to cAMP response element: an alternative cAMP signaling pathway. Proc. Natl. Acad. Sci. USA 95:6687–6692.
22. Dell'Acqua, M. L., and Scott, J. D. (1997) Protein kinase A anchoring. J. Biol. Chem., 272:12881–12884.
23. Pawson, T., and Scott, J. D. (1997) Signaling through scaffold, anchoring, and adaptor proteins. Science, 278: 2075–2080.
24. Tortora, G., Damiano, V., Bianco, C., Baldassarre, G., Bianco, A. R., Lanfrancone, L., Pelicci, P. G., and Ciardiello, F. (1997). The RIa subunit of protein kinase A (PKA) binds to Grb2 and allows PKA interaction with the activated EGF-receptor. Oncogene, 14:923–928.
25. Tournier, S., Raynaud, F., Gerbaud, P., Lohmann, S. M., Doree, M., and Evain-Brion. (1991) Association of Type II cAMP-dependent protein kinase with p34cdc2 protein kinase in human fibroblasts. J. Biol. Chem., 266:19018–19022.
26. Tortora, G., Pepe, S., Bianco, C., Damiano, V., Ruggiero, A., Baldassarre, G., Corbo, C., Cho-Chung, Y. S., Bianco, A. R., and Ciardiello, F. (1994) Differential effects of protein kinase A subunits on Chinese hamster ovary cell cycle and proliferation. Int. J. Cancer., 59:712–716.
27. Tortora, G., Pepe, S., Bianco, C., Baldassarre, G., Budillon, A., Clair, T., Cho-Chung, Y. S., Bianco, A. R., and Ciardiello, F. (1994) The RIα subunit of protein kinase A controls serum dependency and entry into cell cycle of human mammary epithelial cells. Oncogene, 9:3233–3240.
28. Daniel, P. B., Walker, W. H., and Habener, J. F. (1998) Cyclic AMP signaling and gene regulation. Annu. Rev. Nutr. 18:353–383.
29. Naumann, M. and Scheidereit, C. (1994) Activation of NfkB in vivo is regulated by multiple phosphorylations. EMBO J. 13:4597–4607.
30. Neumann, M., Grieshammer, T., Chuvpilo, S., Kneitz, B., Lohoff, M., Schimpl, A., Franza, B. R. Jr, and Serfling, E. (1995) RelA/p65 is a molecular target for the immunosuppressive action of protein kinase A. EMBO J. 14:1991–2004.
31. Cameron, S., Levin, L., Zoller, M., and Wigler, M. (1988) cAMP-independent control of sporulation, glycogen metabolism, and heat shock resistance in S. cerevisiae. Cell 53:555–566.
32. Broach, J. R. And Deschenes, R. J. (1990) The function of RAS genes in Saccharomyces cerevisiae. Adv. Cancer Res. 54:79–138.
33. Gimeno, C. J., Ljungdahl, P. O., Styles, C. A., and Fink, G. R. (1992) Unipolar cell divisions in the yeast S. cerevisiae lead to filamentous growth: regulation by starvation and RAS.Cell 68:1077–1090.
34. Matsumato, K., Uno, I. and Ishikawa, T. (1985) Genetic analysis of the role of cAMP in yeast. Yeast 1:15–24.
35. Cannon, J. F. and Tatchell, K. (1987) Characterization of Saccharomyces cerevisiae genes encoding subunits of cyclic AMP-dependent protein kinase. Mol. Cell. Biol. 7:2653–2663.
36. Toda, T., Cameron, S., Sass, P., Zoller, M., Scott, J. D., McMullen, B., Hurwitz, M., Krebs, E. G. and Wigler, M. Cloning and Characterization of BCY1, a locus encoding a regulatory subunit of the cyclic AMP-dependent protein kinase in Saccharomyces cerevisiae. Mol. Cell. Biol. 7:1371–1377.
37. Toda, T., Cameron, S., Sass, P., Zoller, M. and Wigler, M. (1987) Three different genes in S. cerevisiae encode the catalytic subunits of the cAMP-dependent protein kinase. Cell 50:277–287.
38. Moskvina, E., Imre, E. M., and Ruis, H. (1999) Stress factors acting at the level of the plasma membrane induce transcription via the stress response element (STRE) of the yeast Saccharomyces cerevisiae. Mol. Microbiol. 32:1263–1272.
39. Smith, A., Ward, M. P., and Garrett, S. (1998) Yeast PKA represses Msn2p/Msn4p-dependent gene expression to regulate growth, stress response and glycogen accumulation. EMBO J. 17:3556–3564.
40. Martinez-Pastor, M. T., Marchier, G., Schuller, C., Marchler-Bauer, A., Ruis, H., and Estruch, F. (1996) The Saccharomyces cerevisiae zinc finger proteins Msn2p and Msn4p are required for transcriptional induction through the stress response element (STRE). EMBO J. 15:2227–2235.
41. Schmitt, A. P., and McEntee, K. (1996) Msn2p, a zinc finger DNA-binding protein, is the transcriptional activator of the multistress response in Saccharomyces cerevisiae. Proc. Natl. Acad. Sci. USA 93:5777–5782.
42. Treger, J. M., Magee, T. R., and McEntee, K. (1998) Functional analysis of the stress response element and its role in the multistress response of Saccharomyces cerevisiae. Biochem. Biophys. Res. Commun. 243:13–19.
43. Gorner, W., Durchschlag, E., Martinez-Pastor, M. T., Estruch, F., Ammerer, G., Hamilton, B., Ruis, H., and Schuller, C. (1998) Nuclear localization of the C2H2 zinc finger protein Msn2p is regulated by stress and protein kinase A activity. Genes Dev. 12:586–597.
44. Yang, W.-L., Iacono, L., Tang, W.-M., and Chin, K.-V. (1998) A novel mechanism of cAMP signaling through the interaction of the regulatory subunit of protein kinase A with cytochrome c oxidase subunit Vb. Biochemistry, 37:14175–14180.
45. Abraham, I., Hunter, R. J., Sampson, K. E., Smith, S., Gottesman, M. M., and Mayo, J. K. (1987) Cyclic AMP-dependent protein kinase regulates sensitivity of cells to multiple drugs. Mol. Cell. Biol., 7:3098–3106.
46. Abraham, I., Chin, K.-V., Gottesman, M. M., Mayo, J. and Sampson, K. E. (1990) Transfection of a mutant regulatory subunit gene of cAMP-dependent protein kinase causes increased drug sensitivity and decreased expression of P-glycoprotein. Exp. Cell Res., 189:133–141.
47. Chin, K.-V., Chauhan, S. S., Abraham, I., Sampson, K. E., Krolczyk, A. J., Wong, M., Schimmer, B., Pastan, I., and Gottesman, M. M. (1992) Reduced Expression of the Multidrug Resistant Gene in cAMP-Dependent Protein Kinase Mutant Cell Lines. J. Cell. Physiol., 152:87–94.
48. Fields, S. (1993) The two-hybrid system to detect protein-protein interactions. Methods: A companion to Meth. Enzymol., 5:116–124.
49. Albagli, O., Dhordain, P., Deweindt, C., Lecocq, G., and Leprince, D. (1995) The BTB/POZ domain: a new protein-protein interaction motif common to DNA- and actin-binding proteins. Cell Growth Differ. 6:1193–1198.
50. Reuter, S., Bartelmann, M., Vogt, M., Geisen, C., Napierski, I., Kahn, T., Delius, H., Lichter, P., Weitz, S., Korn, B., and Schwarz, E. (1998) APM-1, a novel human gene, identified by aberrant co-transcription with papillomavirus oncogenes in a cervical carcinoma cell line, encodes a BTB/POZ-zinc finger protein with growth inhibitory activity. EMBO J. 17:215–222.
51. de la Luna, S., Allen, K. E., Mason, S. L., and La Thangue, N. B. (1999) Integration of a growth-suppressing BTB/POZ domain protein with the DP component of the E2F transcription factor. EMBO J. 18:212–228.
52. Okabe, S., Fukuda, T., Ishibashi, K., Kojima, S., Okada, S., Hatano, M., Ebara, M., Saisho, H., and Tokuhisa, T. (1998) BAZF, a novel Bcl6 homolog, functions as a transcriptional repressor. Mol. Cell. Biol. 18:4235–4244.
53. Deweindt, C., Albagli, O., Bernardin, F., Dhordain, P., Quief, S., Lantoine, D., Kerckaert, J. P., and Leprince, D. (1995) The LAZ3/BCL6 oncogene encodes a sequence-specific transcriptional inhibitor: a novel function for the BTB/POZ domain as an autonomous repressing domain. Cell Growth Differ. 6:1495–1503.
54. Yamochi, T., Kaneita, Y., Akiyama, T., Mori, S., and Moriyama, M. (1999) Adenovirus-mediated high expres- 55. Dhordain, P., Albagli, O., Ansieau, S., Koken, M. H., Deweindt, C., Quief, S., Lantoine, D., Leutz, A., Kerckaert, J. P., and Leprince, D. The BTB/POZ domain targets the LAZ3/BCL6 oncoprotein to nuclear dots and mediates homomerisation in vivo. Oncogene 11:2689–2697.
57. Hong, S. H., David, G., Wong, C. W., Dejean, A., Privalsky, M. L. (1997) SMRT corepressor interacts with PLZF and with the PML-retinoic acid receptor alpha (RARalpha) and PLZF-RARalpha oncoproteins associated with acute promyelocytic leukemia. Proc. Natl. Acad. Sci. USA 94:9028–9033.
58. David, G., Alland, L., Hong, S. H., Wong, C. W., DePinho, R. A., and Dejean, A. (1998) Histone deacetylase associated with mSin3A mediates repression by the acute promyelocytic leukemia-associated PLZF protein. Oncogene 16:2549–2556.
59. Kerckaert, J. P., Deweindt, C., Tilly, H., Quief, S., Lecocq, G., and Bastard, C. (1993) LAZ3, a novel zinc-finger encoding gene, is disrupted by recurring chromosome 3q27 translocations in human lymphomas. Nat. Genet. 5:66–70.
60. Ye, B. H., Lista, F., Lo Coco, F., Knowles, D. M., Offit, K., Chaganti, R. S., and Dalla-Favera, R. (1993) Alterations of a zinc finger-encoding gene, BCL-6, in diffuse large-cell lymphoma. Science 262:747–750.
61. Chen, Z., Brand, N. J., Chen, A., Chen, S. J., Tong, J. H., Wang, Z. Y., Waxman, S., and Zelent, A. (1993) Fusion between a novel Kruppel-like zinc finger gene and the retinoic acid receptor-alpha locus due to a variant t(11;17) translocation associated with acute promyelocytic leukaemia. EMBO J. 12:1161–1167.
62. Estruch, F., and Carlson, M. (1993) Two homologous zinc finger genes identified by multicopy suppression in a SNF1 protein kinase mutant of *Saccharomyces cerevisiae*. Mol. Cell. Biol. 13:3872–3881.
63. Deviller, P., Vallier, P., Bata, J., and Saez, J. M. (1984) Distribution and characterization of cAMP-dependent protein kinase isoenzymes in bovine adrenal cells. Mol. Cell. Endocrinol. 38:21–30.
64. Rubin, C. S., Erlichman, J., and Rosen, O. M. (1972) Cyclic adenosine 3',5'-monophosphate-dependent protein kinase of human erythrocyte membranes. J. Biol. Chem. 247:6135–6139.
65. Clegg, C., Correll, L. A., Cadd, G. G., and McKnight, G. S. (1987) Inhibition of intracellular cAMP dependent protein kinase using mutant genes of the regulatory type I subunit. J. Biol. Chem., 262:13111–13119.
66. Chijiwa, T., Mishima, A., Hagiwara, M., Sano, M., Hayashi, K., Inoue, T., Naito, K., Toshioka, T., and Hidaka, H. (1990) Inhibition of forskolin-induced neurite outgrowth and protein phosphorylation by a newly synthesized selective inhibitor of cyclic AMP-dependent protein kinase, N-[2-(p-bromocinnamylamino)ethyl]-5-isoquinolinesulfonamide (H-89), of PC12D pheochromocytoma cells. J. Biol. Chem. 265:5267–5272.

I claim:

1. An isolated polypeptide, comprising SEQ ID NO: 17, wherein said polypeptide is a RIα Interacting Zinc Finger Protein (RIAZ).

2. The poypeptide of claim 1, wherein said polypeptide is encoded by the nucleic acid of SEQ ID NO: 16.

* * * * *